United States Patent [19]
Bru-Magniez et al.

[11] Patent Number: 5,128,359
[45] Date of Patent: * Jul. 7, 1992

[54] BENZIMIDAZOLE AND AZABENZIMIDAZOLE DERIVATIVES WHICH ARE THROMBOXANE RECEPTOR ANTAGONISTS, THEIR METHODS OF PREPARATION

[75] Inventors: Nicole Bru-Magniez, Paris; Eric Nicolai, Caen; Jean-Marie Teulon, La Celle St Cloud, all of France

[73] Assignee: Laboratoires UPSA, France

[ * ] Notice: The portion of the term of this patent subsequent to Jun. 4, 2008 has been disclaimed.

[21] Appl. No.: 650,742

[22] Filed: Feb. 5, 1991

Related U.S. Application Data

[63] Continuation-in-part of Ser. No. 493,880, Mar. 15, 1990, Pat. No. 5,021,443.

[30] Foreign Application Priority Data

Feb. 16, 1990 [FR] France .................. 90 01925

[51] Int. Cl.$^5$ .................. A61K 31/415; C07D 235/12
[52] U.S. Cl. ..................... 514/394; 548/325
[58] Field of Search .................. 548/325; 514/394

[56] References Cited

U.S. PATENT DOCUMENTS 5,021,443 6/1991 Bru-Magniez et al. ............. 548/354

*Primary Examiner*—Robert T. Bond
*Attorney, Agent, or Firm*—Marshall & Melhorn

[57] ABSTRACT

The present invention relates to the derivatives of the formula

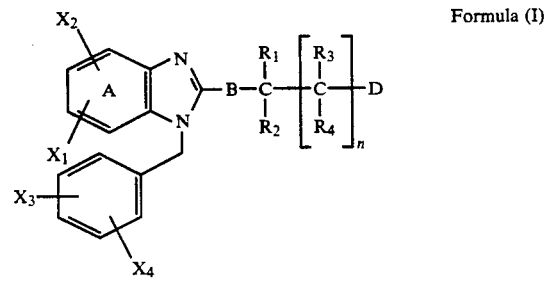

Formula (I)

where the substituents are defined in the specification. These compounds possess thromboxane receptor antagonist properties.

15 Claims, No Drawings

BENZIMIDAZOLE AND AZABENZIMIDAZOLE DERIVATIVES WHICH ARE THROMBOXANE RECEPTOR ANTAGONISTS, THEIR METHODS OF PREPARATION

CROSS REFERENCE TO EARLIER APPLICATION

This application is a CIP of Ser. No. 07/493,880, filed March 15, 1990 now U.S. Pat. No. 5,021,443, granted 4 June 1991.

The present invention relates, by way of novel products, to the benzimidazole and azabenzimidazole derivatives of general formula (I) below and to their salts.

The compounds in question have a very valuable pharmacological profile insofar as they possess thromboxane receptor antagonist properties. Thromboxane $A_2$ (or $TXA_2$) affects a variety of tissues or cells. A constrictive action is observed on the vascular, bronchial and uterine smooth musculature. The blood platelets are aggregated by $TXA_2$, while the membranes of the circulating cells are modified and can thus adhere to each other. The different properties described for thromboxane $A_2$ are such that a $TXA_2$ receptor antagonist may be envisaged as having a favorable role in the following pathological conditions: myocardial infarction, angina pectoris, stroke, migraine, brain hemorrhage, atherosclerosis, pulmonary embolism, bronchial asthma, bronchitis, pneumonia, circulatory shock of various origins (hemorrhage, septicemia, heart failure, trauma, acute pancreatitis, burn, bacterial origin), nephritis, graft rejection and cancerous metastases.

The present invention further relates to the method of preparing said products and to their applications in therapy. It further relates to the novel intermediates which make it possible to synthesize said products.

These benzimidazole and azabenzimidazole derivatives have general formula (I):

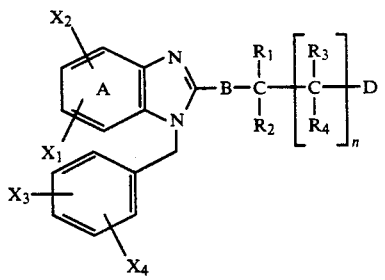

Formula (I)

in which:

A is an aromatic ring or a nitrogen heterocycle;

$X_1$, $X_2$, $X_3$ and $X_4$ are independently a hydrogen atom, a halogen atom, a lower alkyl radical, a $C_3$-$C_7$ lower cycloalkyl radical, an alkoxy radical, an alkylthio radical, a sulfone group, $SO_2$-lower alkyl, a sulfoxide group, SO-lower alkyl, a trifluoromethyl group, a nitro group, a hydroxyl group, a methylene alcohol radical or a group COOR', in which R, is a hydrogen or a lower alkyl; $X_3$ and $X_4$ can also form a naphthalene with the phenyl;

B is $CR_5R_6$, $R_5$ and $R_6$ being a hydrogen atom, a lower alkyl or a $C_3$-$C_7$ cycloalkyl radical, or the sulfur atom;

$R_1$, $R_2$, $R_3$ and $R_4$ are independently a hydrogen atom, a lower alkyl radical or a $C_3$-$C_7$ cycloalkyl radical; $CR_1R_2$ or $CR_3R_4$ can form with B, when the latter is $CR_5R_6$, a cycloalkyl or a cycloalkene having 3 to 7 carbon atoms; $R_1R_2$ and $R_3R_4$ can also form a ring having 3 to 7 carbon atoms;

n is an integer from 1 to 4 and can be 0 if $R_1$ and $R_2$ are other than hydrogen; and D is a chemical group which can be: $COOR_7$, $R_7$ being the hydrogen atom, a lower alkyl radical or a $C_3$-$C_7$ cycloalkyl radical, $CONH$-$R_8$, $R_8$ being the hydrogen atom, a lower alkyl radical or a $C_3$-$C_7$ cycloalkyl radical, or CN.

In the description and the claims, lower alkyl radical is understood as meaning a linear or branched hydrocarbon chain having 1 to 6 carbon atoms. A lower alkyl radical is, for example, a methyl, ethyl, propyl, isopropyl, butyl, isobutyl, tert-butyl, pentyl, isopentyl, hexyl or isohexyl radical.

$C_3$-$C_7$ cycloalkyl radical is understood as meaning a saturated cyclic radical, preferably a cyclopropane, cyclobutane, cyclopentane, cyclohexane or cycloheptane radical.

$C_3$-$C_7$ cycloalkene radical is understood as meaning a cyclic radical possessing an unsaturation, preferably a cyclobutene, cyclopentene, cyclohexene or cycloheptene radical.

Alkoxy radical is understood as meaning an O-lower alkyl group and alkylthio radical is understood as meaning an S-lower alkyl group, lower alkyl being as defined above.

In the description and the claims, halogen is understood as meaning a chlorine, bromine, iodine or fluorine atom.

Aromatic ring is understood as meaning any aromatic ring such as benzene or naphthalene.

Nitrogen heterocycle is understood as meaning any aromatic ring containing from one to four nitrogens in the ring. Pyridine will be preferred in particular among the nitrogen-containing rings.

The derivatives most similar to these compounds which have so far been disclosed in the literature are described in patent n° 1.580.823 filed in France on 1 December 1967 under US priority of 2 December 1966, n° 598 607, in the name of T. Y. SHEN, A. R. MATZUK and H. SHAM (MERCK and CO.). Said patent describes benzimidazoles substituted in either the 1-position or the 2-position by a lower alkanoic acid residue and in the other position by an aromatic or heteroaromatic group having fewer than three fused rings.

The lower alkanoic acid residue is limited to a chain length of two carbons and can be: $—CH_2—$, $—CH_2—CH_2—$ or $—CH(CH_3)—CH_2—$.

These derivatives are described as antiinflammatories and antipyretics.

The Applicant has found that these compounds are only sliqhtly active, if at all, as thromboxane receptor antagonists.

In fact, the length of the chain which carries the acid group, namely one or two carbon atoms, is insufficient to exhibit a suitable affinity for the receptor.

On the other hand, surprisingly, the Applicant has demonstrated that if this chain possesses more than three carbon atoms or a heteroatom such as sulfur and at least three carbon atoms, and optimally if it is a branched chain having five carbons, the affinity for the receptor is such that it makes it possible to obtain very good $TXA_2$ antagonists.

Variants of the invention form the subject of the sub-claims. In particular, according to these variants, A can be a phenyl ring or a pyridine ring and $X_1$ can be a fluorine atom or a chlorine atom. Likewise, $X_3$ can be a chlorine atom, a methoxy group or a methylthio group; $X_4$ can be a chlorine atom; D can advantageously be an acid group.

Also according to a particular variant, B can be a methylene group, $R_1$ and $R_2$ are each a methyl, $R_3$ and $R_4$ are hydrogen and n is equal to 1.

According to another advantageous variant, B is the sulfur atom.

According to yet another variant, C and $R^1$ and $R^2$ are a cyclopentane.

The particularly preferred compounds of the invention are those selected from the products of the formulae

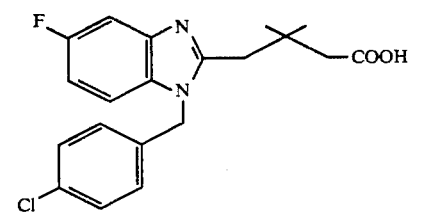

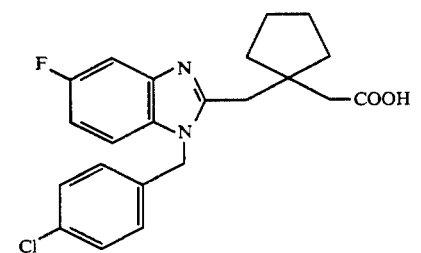

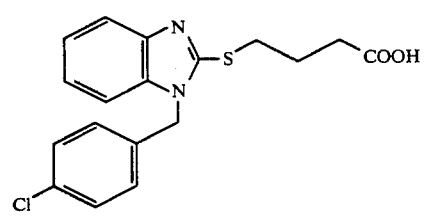

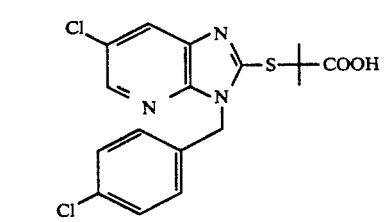

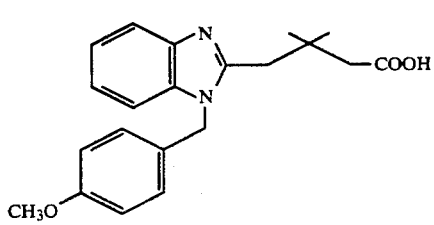

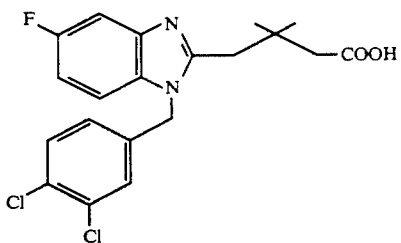

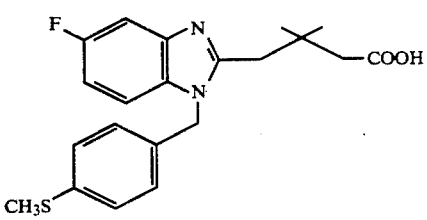

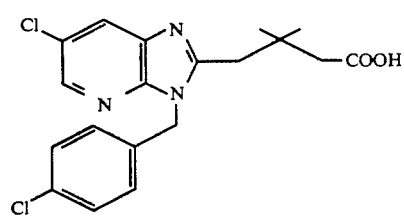

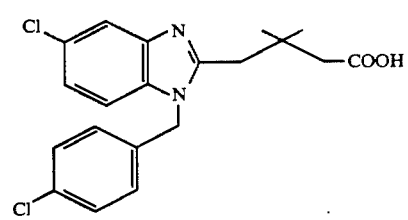

A—A method of preparing the compunds of formula (I) in which B is the sulfur atom According to the invention, the compounds of formula (I) in which B is the sulur atom and D ios a group $COOR_7$, $X_1$, $X_2$, $X_3$, $X_4$, $R_1$, $R_2$, $R_3$, $R_4$ and n being as defined above and $R^7$ being a lower alkyl radical, can be synthesized by reacting an alkyl halogenoalkanoate of formula (II):

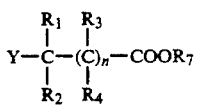

Formula (II)

in which $R^1$, $R^2$, $R^3$, $R^4$, n and $R^7$ are as defined above and Y is a halogen, optimally chlorine or bromine, with a mercaptobenzimidazole or mercaptoazabenzimidazole derivative of formula (III):

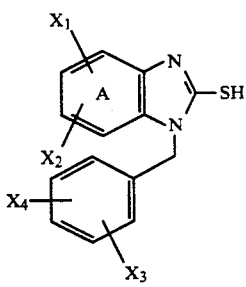

Formula (III)

in which A, $X_1$, $X_2$, $X_3$ and $X_4$ are as defined above, in the presence of a base such as a sodium or potassium alcoholate in an alcohol, sodium hydride in dimethylformamide or potassium carbonate in acetone or butan-2-one.

The compounds of formula (III) are synthesized by reacting carbon disulfide or potassium xanthogenate with diamine compounds of formula (IV):

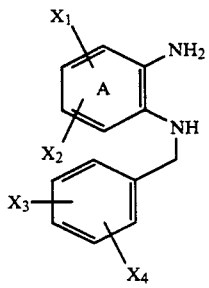

Formula (IV)

in which A, $X_1$, $X_2$, $X_3$ and $X_4$ are as defined above, under reflux in a solvent such as an alcohol.

The compounds of formula (IV) can be obtained by catalytic hydrogenation of the nitro derivatives of formula (V):

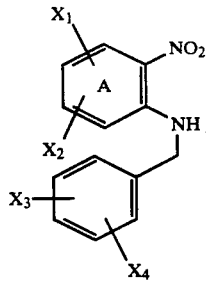

Formula (V)

in which A, $X_1$, $X_2$, $X_3$ and $X_4$ are as defined above, in the presence of Raney nickel for example, in solvents such as an alcohol, tetrahydrofuran or 2-methoxyethanol, under pressure or at atmospheric pressure and at a temperature of between 20° and 120° C.

These nitro derivatives of formula (V) can be synthesized by reacting a substituted benzylamine of formula (VI):

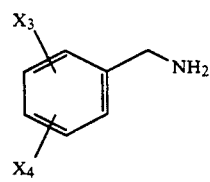

Formula (VI)

in which $X_3$ and $X_4$ are as defined above, with a halogenated nitro derivative of formula (VII):

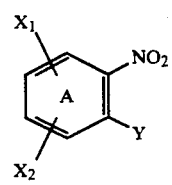

Formula (VII)

in which A, $X_1$ and $X_2$ are as defined above and Y is a halogen atom, optimally chlorine or fluorine.

In the case where A is a phenyl, the reaction can be carried out in a solvent such as an alcohol or tetrahydrofuran, in the presence of potassium carbonate, or simply by heating the reactants at 135° C., without a solvent or a base, according to the method described in Belgian patent 667,333 of 24 January 1966.

In the case where A is a nitrogen heterocycle, for example pyridine or pyrimidine, the reaction may be carried out in solvents such as toluene or xylene, in the presence or absence of pyridine or 2-methyl-5-ethyl-pyridine.

The benzylamines of formula (VI) are commercially available or can be prepared by:
- hydrogenation of the corresponding Schiff base obtained by reacting ammonia with the corresponding aldehyde under pressure;
- hydrogenation of the corresponding oxime obtained by reacting hydroxylamine with the corresponding aldehyde; or
- Hofmann degradation of the corresponding phenylacetamide, i.e. treatment with a solution of a hypohalite, for example sodium hypobromite.

The orthohalogenated nitro derivatives of formula (VII) are commercially available or can be synthesized according to methods described in the literature, for example in the following references: in the case where A is a phenyl:

HOLLEMAN; REIDING; Rec Trav. Chim. Pays Bas 1904, 23, 361

SWARTS; Rec. Trav. Chim. Pays Bas 1916, 35. 155 in the case where A is a nitrogen heterocycle:

BATKOWSKI, T.; Rocz Chem. 1968, 42 (12), 2079–88

BEBENBURG, W.; STEIMMETZ, S.; THIELE, K.; Chemiker Zeitung 1979, 103 (12), 387–99

BOON, W. R.; JONES, W. G. M.; RAMAGE, G. R.; J. Chem. Soc. 1951, 96

KRUGER, S.; MANN, F.G.; J. Chem. Soc. 1955, 2755

FUJIMATO, M.; Pharm. Bull. (Tokyo) 1956, 4, 340

The nitro compounds of formula (V) in which A is a phenyl can also be prepared in several steps from nitroanilines of formula (VII) in which A is a phenyl and Y=NH$_2$. In a first stage, these nitroanilines are treated with tosyl chloride in pyridine. The resulting sulfonamide is then alkylated with an appropriately substituted benzyl chloride in the presence of a metalating agent such as sodium hydride, in a solvent such as dimethylformamide. The tosylate (4-methylbenzenesulfonyl) group is then hydrolyzed in propionic acid, in the presence of concentrated sulfuric acid, to give the corresponding nitro derivatives of formula (V).

Another variant of the method of synthesizing these compounds of formula (V) in which A is a phenyl consists in heating the same nitroanilines with appropriately substituted benzyl chlorides or bromides to a temperature of between 100° and 130° C., without a solvent and in the presence of dry sodium acetate and iodine.

B—Method of oreparinc the compounds of formula (I) in which B is a qroup $CR_5R_6$ The derivatives of formula (I) in which B is a group $CR_5R_6$ and D is a group CN or $COOR_7$, A, $X_1$, $X_2$, $X_3$, $X_4$, $R_1$, $R_2$, $R_3$, $R_4$, $R_5$, $R_6$ and n being as defined above and $R_7$ being a lower alkyl group, can be synthesized by reacting derivatives of formula (IV) with derivatives of formula (VIII):

Formula (VIII)

$$ClCO-\underset{\underset{R_6}{|}}{\overset{\overset{R_5}{|}}{C}}-\underset{\underset{R_2}{|}}{\overset{\overset{R_1}{|}}{C}}-\left[\underset{\underset{}{|}}{\overset{\overset{R_3}{|}}{C}}\underset{R_4}{}\right]_n-D$$

in which D, $R_1$, $R_2$, $R_3$, $R_4$, $R_5$, $R_6$ and n are as defined above and $R_7$ is a lower alkyl radical.

These derivatives of formula (VIII) can be prepared, according to a classical method of forming acid chlorides, by treating the corresponding acid ester or cyano acid derivatives of formula (IX):

Formula (IX)

$$HOOC-\underset{\underset{R_6}{|}}{\overset{\overset{R_5}{|}}{C}}-\underset{\underset{R_2}{|}}{\overset{\overset{R_1}{|}}{C}}-\left[\underset{R_4}{\overset{R_3}{C}}\right]_n-D$$

in which D, $R_1$, $R_2$, $R_3$, $R_4$, $R_5$, $R_6$ and n are as defined above and $R_7$ is a lower alkyl radical, with thionyl chloride or phosphorus oxychloride for example, in a solvent such as toluene for example, or without a solvent.

These compounds of formula (IX) are obtained by different routes:

by monosaponification of the corresponding diesters or hydrolysis of the corresponding cyano esters in the presence of one equivalent of sodium hydroxide, according to a procedure described for example in the following reference:

LE MOAL H.; FOUCAUD A.; CARRIE R.; DANION D. and FAYAT C.; Bull. Soc. Chim. Fr. 1964, 828 in another route for the preparation of the acid ester derivatives, by treatment of the corresponding acid anhydride derivatives with an alcohol. The acid anhydrides are obtained by dehydration of the corresponding diacids with acetic anhydride under reflux, or by treatment with half an equivalent of dicyclohexylcarbodiimide. The preparation of the diacid derivatives used which are not commercially available may be found in the following references:

HOWARD E. ZIMMERMAN; DAVID N. SCHISSEL; J. Org. Chem. 1986, 51, 196-207

H. NAJER; R. GIUDICELLI; J. SETTE; Bull. Soc. Chim. Fr. 1964, 2572-2581

J. SEYDEN PENNE; M. C. ROUX-SCHMITT; Bull. Soc. Chim. Fr. 1968, 3812

N. L. ALLINGER; M. NAKAZAKI; V. ZALKOW; J. Am. Chem. Soc. 1959, 81, 4074-4080

J. MEINWALD; J. J. TUFARIELLO; J. J. HURST; J. Am. Chem. Soc. 1964, 86, 2914-2920

This reaction between the acid chloride esters or the cyano acid chlorides of formula (VIII) and the diamino derivatives of formula (IV) is performed in two steps.

In a first stage, in a solvent such as chloroform or tetrahydrofuran for example, in the presence of triethylamine or pyridine, it yields a mixture of amide compounds of formulae (X) and (X bis):

Formula (X)

Formula (X bis)

in which A, D, $X_1$, $X_2$, $X_3$, $X_4$, $R_1$, $R_2$, $R_3$, $R_4$, $R_5$, $R_6$ and n are defined above.

This mixture of amide compounds of formulae (X) and X bis) is then treated in an acid medium, either with concentrated hydrochloric acid in an alcohol under reflx, or with concentrated sulfuric acid, or with polyphosphoric acid, to give the compounds of formula (I) in which B is a group $CR_5R_6$ and D is a group CN or $CO_2R_7$, $R^7$ being a lower alkyl radical.

The compounds of formula (I) in which B is a group $CR_5R_6$ and D is a group $CO_2R_7$ or CN, $R_7$ being a lower alkyl radical and $R_5$ and $R_6$ being as defined above, can also be prepared in the following manner:

Reaction of aldehydes of formula (VIII'):

Formula (VIII')

$$OHC-\underset{\underset{R_6}{|}}{\overset{\overset{R_5}{|}}{C}}-\underset{\underset{R_2}{|}}{\overset{\overset{R_1}{|}}{C}}-\left[\underset{R_4}{\overset{R_3}{C}}\right]_n-D$$

in which $R_1$, $R_2$, $R_3$, $R_4$, $R_5$, $R_6$, n and D are as defined above, with the compounds of formula (IV) in a mixture of acetic acid and ethanol gives derivatives of formula (X'):

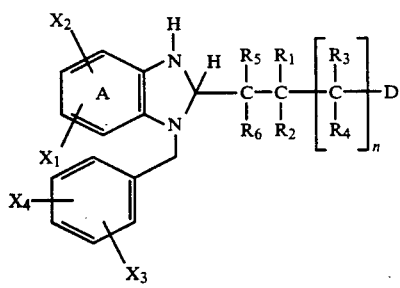

Formula (X')

in which $X_1$, $X_2$, $X_3$, $X_4$, $R_1$, $R_2$, $R_3$, $R_4$, $R_5$, $R_6$, n and D are as defined above.

Treatment of these compounds of formula (X') with an oxidizing agent such as iodine or barium manganate for example, at a temperature ranging from room temperature to 100° C., will give the compounds of formula (I) in which B is a group $CR_5R_6$ and D is a group $CO_2R_7$ or CN, $R_7$ being a lower alkyl radical and $R_5$ and $R_6$ being as defined above. Examples of this kind of reaction may be found in the following references:

Srivastava, R. G.; Venkataramani, P. S.; Synt. Comm. 1988, 18 (13), 1537–1544

Perumattam, G.; Synt. Comm. 1989, 19 (19), 3367–3370

The aldehydes of formula (VIII') can be prepared by catalytic hydrogenation of the acid chloride derivatives (VIII) in which D is an ester group, in the presence of palladium-on-charcoal and lutidine in tetrahydrofuran.

This method is particularly advantageous when the ring A is a pyridine ring.

The compounds of formula (I) in which A is a phenyl and D is the group CN or $CO_2R_7$, $R_7$ being a lower alkyl radical, can also be synthesized by reacting an appropriately substituted benzyl chloride with derivatives of formula (XI):

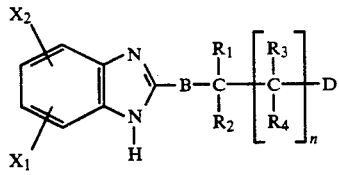

Formula (XI)

in which D, $X_1$, $X_2$, $R_1$, $R_2$, $R_3$, $R_4$, B and n are as defined above, in a solvent such as dimethylformamide, in the presence of a metalating agent such as sodium hydride.

The compounds of formula (XI) in which B is the sulfur atom can be synthesized from the compounds of formula (XII):

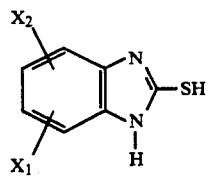

Formula (XII)

in which $X_1$ and $X_2$ are as defined above, with alkyl halogenoalkanoate compounds of formula (II) in the presence of a base such as sodium ethylate in alcohol or potassium carbonate in acetone or tetrahydrofuran.

The compounds of formula (XII) are commercially available or are synthesized according to methods described in BEILSTEIN 24, 119 and 24, supplement (3), 293.

The compounds of formula (XI) in which B is a group $CR_5R_6$, $R_5$ and $R_6$ being as defined above, can be synthesized by reacting an acid chloride ester compound of formula (VIII) with an orthophenylenediamine compound of formula (XIII):

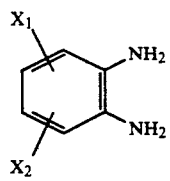

Formula (XIII)

in which $X_1$ and $X_2$ are as defined above, under conditions identical to those described above for reacting the compounds of formula (IV) with the derivatives of formula (VIII).

The compounds of formula (XIII) are commercially available.

The compounds of formula (I) in which D is the group $COOR_7$ and $R_7$ is the hydrogen atom are obtained by classical hydrolysis of the compounds of formula (I) in which D is the group $COOR_7$ and $R_7$ is a lower alkyl radical, or D is the group CN, either in an acid medium or in a basic medium.

The compounds of formula (I) in which D is a group $CONH-R_8$ are obtained by reacting amines of the formula $R_8-NH_2$, $R_8$ being as defined above, with acid chlorides of formula (XIV):

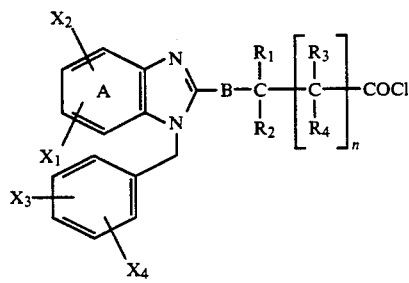

Formula (XIV)

in which A, $X_1$, $X_2$, $X_3$, $X_4$, $R_1$, $R_2$, $R_3$, $R_4$, B and n are as defined above, in a solvent such as chloroform or tetrahydrofuran, in the presence of excess amine or of triethylamine or pyridine. In the case where $R_8$ is hydrogen, it will be possible quite simply to react the acid chloride of formula (XIV) with a solution of ammonia.

The compounds of formula (XIV) can be prepared according to a classical method for acid chlorides, namely by reacting thionyl chloride, oxalyl chloride or phosphorus oxychloride with the corresponding compounds of formula (I) in which D is the group $CO_2H$.

The compounds of formula (I) in which D is the group CN can also be prepared by dehydration of the corresponding amide compounds, in which D is $CONH_2$, by treatment with phosphorus oxychloride for example, in a solvent such as dimethylformamide or without a solvent.

Addition salts of some of the compounds of formula (I) can be obtained, especially pharmaceutically acceptable addition salts. The sodium, potassium and calcium salts may be mentioned in particular when D is an acid group.

The novel compounds according to the invention possess remarkable pharmacological properties as thromboxane receptor antagonists and can be used in therapy for the treatment of myocardial infarction, angina pectoris, stroke, migraine, cerebral hemorrhages, atherosclerosis, pulmonary embolism, bronchial asthma, bronchitis, pneumonia, circulatory shocks of various origins, nephritis, graft rejection and cancerous metastases.

Thus the invention also covers a pharmaceutical composition which comprises a pharmaceutically effective amount of at least one compound of formula (I) as defined above, as well as its pharmaceutically acceptable addition salts if appropriate, which may or may not be incorporated in a pharmaceutically acceptable excipient, vehicle or carrier.

The invention also covers a pharmaceutical composition active as a thromboxane receptor antagonist, with which the following diseases in particular can be favorably treated: myocardial infarction, angina pectoris, stroke, migraine, cerebral hemorrhage, atherosclerosis, pulmonary embolism, bronchial asthma, bronchitis, pneumonia, circulatory shocks of various origins such as hemorrhage, septicemia, heart failure, trauma, acute pancreatitis, burn or bacterial origin, nephritis, graft rejection and cancerous metastases, said composition comprising a pharmaceutically effective amount of at least one compound of formula (I) mentioned above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, as well as its pharmaceutically acceptable addition salts if appropriate, into a pharmaceutically acceptable excipient, vehicle or carrier.

In another embodiment, a pharmaceutical composition active as a thromboxane receptor antagonist is prepared with which the following diseases in particular can be favorably treated: myocardial infarction, angina pectoris, stroke, migraine, cerebral hemorrhage, atherosclerosis, pulmonary embolism, bronchial asthma, bronchitis, pneumonia, circulatory shocks of various origins such as hemorrhage, septicemia, heart failure, trauma, acute pancreatitis, burn or bacterial origin, nephritis, graft rejection and cancerous metastases.

In another variant, a pharmaceutical composition is formulated as gelatin capsules or tablets containing from 1 to 200 mg of active ingredient, or as injectable preparations containing from 0.01 to 10 mg of active ingredient.

The invention also covers a method of therapeutic treatment for mammals, which comprises administering to said mammal a therapeutically effective amount of at least one compound of formula (I) as defined above, or one of its pharmaceutically acceptable addition salts, which may or may not be incorporated in a pharmaceutically acceptable excipient, vehicle or carrier. In a variant of this method of treatment, the compound of formula (I), either by itself or in association with a pharmaceutically acceptable excipient, is formulated as gelatin capsules or tablets containing from 1 to 200 mg of active ingredient for oral administration, or as injectable preparations containing from 0.01 to 10 mg of active ingredient for parenteral administration.

In human and animal therapy, the compounds of formula (I) and their salts can be administered, by themselves or in association with a physiologically acceptable excipient, in any form, in particular in the form of gelatin capsules and tablets for oral administration or in the form of an injectable solution for parenteral administration.

As will become clearly apparent from the pharmacology tests given at the end of the description, the compounds according to the invention can be administered in human therapy, for the above-mentioned indications, orally in the form of tablets or gelatin capsules containing from 1 to 200 mg of active ingredient, or parenterally in the form of injectable preparations containing from 0.01 to 10 mg of active ingredient, in one or more dosage units per day for an adult with an average weight of 60 to 70 kg.

In animal therapy, the daily dose which can be used should normally be between 1 and 100 mg per kg.

Further characteristics and advantages of the invention will be understood more clearly from the following description of some Preparatory Examples, which in no way imply a limitation but are given by way of illustration.

EXAMPLE 1

2-(4-Chlorophenylmethylamino)-5-fluoronitrobenzene

Formula (V): $X_1=5\text{-}F$, $X_2=X_3=H$, $X_4=4\text{-}Cl$, $A=$phenyl 30 g of 2,5-difluoronitrobenzene and 26.7 g of 4-chlorobenzylamine are dissolved in 300 ml of tetrahydrofuran. 40 g of potassium carbonate are added to this solution and the mixture is refluxed for 8 hours. After cooling, the reaction mixture is added to 1.7 l of water and 50 ml of concentrated hydrochloric acid. The crystals obtained are filtered off and washed with water and then with isopropyl ether to give 41.9 g of 2-(4-chlorophenylmethylamino)-5-fluoronitrobenzene in the form of crystals melting at 160° C.

The following Example was synthesized by this procedure:

EXAMPLE 2

2-(3,4-Dichlorophenylmethylamino)-5-fluoronitrobenzene

Formula (V): $X_1=5\text{-}F$, $X_2=H$, $X_3=3\text{-}Cl$, $X_4=4\text{-}Cl$, $A=$phenyl Crystals melting at 110° C.

EXAMPLE 3

2-(4-Chlorophenylmethylamino)-5-chloronitrobenzene

Formula (V): $X_1=5\text{-}Cl$, $X_2=H$, $X_3=4\text{-}Cl$, $X_4=H$, $A=$phenyl 25 g of 2,5-dichloronitrobenzene and 36.9 g of 4-chlorobenzylamine are heated for two hours at 135° C., it being necessary for the temperature always to be kept below 140° C. After cooling, the mixture is taken up with water and extracted with ethyl acetate. After drying over magnesium sulfate and evaporation under vacuum, the residue is taken up with ether and the crystals obtained are filtered off and washed with ether to give 22.3 g of 2-(4-chlorophenylmethylamino)-5-chloronitrobenzene in the form of crystals melting at 120° C.

EXAMPLE 4

2-(4-Chlorophenylmethylamino)-5-methoxynitrobenzene

Formula (V): $X_1=5$-OMe, $X_2=H$, $X_3=4$-Cl, $X=H$, A=phenyl

A) 2-(4-Methylphenylsulfonylamino)-5-methoxynitrobenzene 50 g of 4-methoxy-2-nitroaniline are stirred at 0° C. in 300 ml of pyridine. 56.7 g of tosyl chloride are added in portions at 0° C. and the mixture is then stirred for two hours at room temperature, left to stand overnight and poured into an ice/water mixture. The crystals obtained are filtered off and washed with water and then with isopropyl ether to give 72.8 g of 2-(4-methylbenzenesulfonylamino)-5-methoxynitrobenzene in the form of crystals melting at 99° C.

B) N-(4-Chlorobenzyl)-N-(4-methylbenzenesulfonyl)-2-nitro-4-methoxyaniline 72.8 g of 2-(4-methylbenzenesulfonylamino)-5-methoxynitrobenzene, prepared in A), are added to 56.5 ml of 4 N sodium hydroxide solution and 29.2 g of 4-chlorobenzyl chloride. The mixture is refluxed for 4 hours, a further 43.7 g of 4-chlorobenzyl chloride are then added and the resulting mixture is refluxed for another 45 minutes. After cooling, 12.2 ml of 35% sodium hydroxide solution are added to the reaction mixture, the latter is refluxed for three hours 45 minutes and then cooled and water and ether are added. The insoluble material is filtered off and washed with water and ether to give 98 g of N-(4-chlorobenzyl)-N-(4-methylbenzenesulfonyl)-2-nitro-4-methoxyaniline in the form of crystals melting at 124° C. Evaporation of the ether phase yields an additional 10 g of crystals melting at 124° C.

C) 2-(4-Chlorophenylmethylamino)-5-methoxynitrobenzene 108 g of N-(4-chlorobenzyl)-N-(4-methylbenzenesulfonyl)-2-nitro-4-methoxyaniline, prepared in B), are added to 940 ml of propionic acid and 102 ml of concentrated sulfuric acid. The mixture is heated at 95° C. for 1 h 30 min and the solution is concentrated to half its volume by evaporation under vacuum and then poured on to ice and neutralized with ammonium hydroxide.

The crystals obtained are filtered off and washed with water and then with isopropyl ether to give 60 g of 2-(4-chlorophenylmethylamino)-5-methoxynitrobenzene in the form of crystals melting at 135° C.

EXAMPLE 5

2-(4-Chlorophenylmethylamino)-3-nitropyridine

Formula (V): $X_3=4$-Cl, $X_1=X_2=X_4=H$, A=2-pyridine

A solution of 26.5 g of 2-chloro-3-nitropyridine, 23.7 g of 4-chlorobenzylamine and 25 ml of 2-methyl-5-ethylpyridine in 200 ml of xylene is refluxed for 12 hours. The reaction mixture is then cooled, water and acetic acid are added and the resulting mixture is then extracted with ether. The organic phase is dried over magnesium sulfate, filtered and then evaporated under vacuum to give an oil which crystallizes from isopropyl ether. The crystals are filtered off and then dried to give 27 of 2-(4-chlorophenylmethylamino)-3-nitropyridine in the form of crystals melting at 100° C.

EXAMPLE 6

2-(4-Chlorophenylmethylamino)-3-nitro-5-chloropyridine

Formula (V): $X_1=5$-Cl, $X_2=H$, $X_3=4$-Cl, $X_4=H$, A=2-pyridine

A solution of 20.9 g of 4-chlorobenzylamine and 15.7 g of 2,5-dichloro-3-nitropyridine in 250 ml of xylene and 20 ml of 2-methyl-5-ethylpyridine is refluxed for 30 hours. After cooling, water is added to the reaction mixture, the resulting mixture is then extracted with ethyl acetate and the organic phase is washed with a dilute solution of hydrochloric acid and dried over magnesium sulfate. The solvent is evaporated off under vacuum and the residue obtained crystallizes from isopropyl ether to give 21.1 g of 2-(4-chlorophenylmethylamino)-3-nitro-5-chloropyridine in the form of crystals melting at 120° C.

EXAMPLE 7

2-(2-Fluoro-4-bromophenylmethylamino)-3-nitro-5-chloropyridine

Formula (V): $X_1=5$-Cl, $X_2=H$, $X_3=2$-F, $X_4=4$-Br, A=2-pyridine

Prepared by the procedure of Example 6.

Crystals melting at 75°–77° C.

EXAMPLE 8

2-(4-Chlorophenylmethylamino)-5-fluoroaniline

Formula (IV): $X_1=5$-F, $X_2=H$, $X_3=4$-Cl, $X_4=H$, A=phenyl 41.7 g of 2-(4-chlorophenylmethylamino)-5-fluoronitrobenzene, prepared in Example 1, are dissolved in 1 l of tetrahydrofuran and hydrogenated at ordinary temperature and pressure in the presence of 5 g of Raney nickel. When the theoretical amount of hydrogen has been absorbed, the catalyst is filtered off and the solvent is evaporated off under vacuum to give 34.1 g of 2-(4-chlorophenylmethylamino)-5-fluoroaniline in the form of crystals melting at 99° C.

The following Examples were prepared by the same procedure:

EXAMPLE 9

2-(4-Chlorophenylmethylamino)-5-methoxyaniline

Formula (IV): $X_1=5$-MeO, $X_2=H$, $X_3=4$-Cl, $X_4=H$, A=phenyl

Crystals melting at 90° C.

EXAMPLE 10

2-(3,4-Dichlorophenylmethylamino)-5-fluoroaniline

Formula (IV): $X_1=5$-F, $X_2=H$, $X_3=3$-Cl, $X_4=4$-Cl, A=phenyl

Crystals melting at 104° C.

EXAMPLE 11

2-(4-Chlorophenylmethylamino)-5-chloroaniline

Formula (IV): $X_1=5$-Cl, $X_2=H$, $X_3=4$-Cl, $X_4=H$, A=phenyl

Crystals melting at 138° C.

EXAMPLE 12

2-(2-Fluoro-4-bromophenylmethylamino)-3-amino-5-chloropyridine

Formula (IV): $X_1=5$-Cl, $X_2=H$, $X_3=2$-F, $X_4=4$-Br, $A=2$-pyridine
Crystals melting at 97° C.

EXAMPLE 13

2-(4-Chlorophenylmethylamino)-3-aminopyridine

Formula (IV): $X_1=H$, $X_2=H$, $X_3=4$-Cl, $X_4=H$, $A=2$-pyridine
Crystals melting at 132° C.

EXAMPLE 14

2-(4-Chlorophenylmethylamino)-3-amino-5-chloropyridine

Formula (IV): $X_1=5$-Cl, $X_2=H$, $X_3=4$-Cl, $X_4=H$, $A=2$-pyridine
Oil used as such for the next step.

EXAMPLE 15

1-(4-Chlorophenylmethyl)-2-mercapto-5-fluorobenzimidazole

Formula (III): $X_1=5$-F, $X_2=H$, $X_3=4$-Cl, $X_4=H$, $A=$phenyl 25 ml of carbon disulfide are added to 35.2 g of 2-(4-chlorophenylmethylamino)-5-fluoroaniline, prepared in Example 8, dissolved in 500 ml of ethanol. The mixture is refluxed for 12 hours and allowed to return to room temperature. After standing for a few hours, the crystals are filtered off and washed with ethanol and then with isopropanol and ether to give 33 g of 1-(4-chlorophenylmethyl)-2-mercapto-5-fluorobenzimidazole in the form of crystals melting at 215° C.

The following Examples were prepared by the same procedure:

EXAMPLE 16

1-(4-Chlorophenylmethyl)-2-mercaptoimidazo[4,5-b]pyridine

Formula (III): $X_3=4$-Cl, $X_1=X_2=X_4=H$, $A=2$-pyridine
Crystals meltinq at 216° C.

EXAMPLE 17

1-(4-Chlorophenylmethyl)-2-mercapto-5-chloroimidazo[4,5-b]pyridine

Formula (III): $X_1=5$-Cl, $X_2=H$, $X_3=4$-Cl, $X_4=H$, $A=2$-pyridine
Crystals melting at 260° C.

EXAMPLE 18

1-(2-Fluoro-4-bromophenylmethyl)-2-mercapto-5-chloropyridine

Formula (III): $X_1=5$-Cl, $X_2=H$, $X_3=2$-F, $X_4=4$-Br, $A=2$-pyridine
Crystals melting at 240° C.

EXAMPLE 19

Ethyl 4-[1-(4-chlorobenzyl)-5-fluorobenzimidazol-2-yl]mercaptobutanoate

Formula (I): $X_1=5$-F, $X_2=H$, $X_3=4$-Cl, $X_4=H$, $A=$phenyl, $B=S$, $D=CO_2Et$, $R_1=R_2=R_3=R_4=H$, $n=2$ 9 g of 1-(4-chlorophenylmethyl)-2-mercapto-5-fluorobenzimidazole, prepared in Example 15, and 4.4 ml of ethyl 4-bromobutyrate are refluxed for 5 hours in 100 ml of acetone in the presence of 6.3 g of potassium carbonate. The solvent is evaporated off under vacuum, the residue is taken up with water and then extracted with ethyl acetate and the extract is washed with a dilute solution of sodium hydroxide. The organic phase is dried over magnesium sulfate and evaporated under vacuum to give 11.9 g of ethyl 4-[1-(4-chlorobenzyl)-5-fluorobenzimidazol-2-yl]mercaptobutanoate in the form of an oil, which is used as such for the next step.

The following Examples were prepared by the same procedure:

EXAMPLE 20

Ethyl 5-[1-(4-chlorobenzyl)-5-fluorobenzimidazol-2-yl]mercaptopentanoate

Formula (I): $X_1=5$-F, $X_2=H$, $X_3=4$-Cl, $X_4=H$, $A=$phenyl, $B=S$, $D=CO_2Et$, $R_1=R_2=R_3=R_4=H$, $n=3$
Oil used as such for the next step.

EXAMPLE 21

Ethyl 4-[1-(2-fluoro-4-bromobenzyl)-5-chloroimidazo[4,5-b]pyridin-2-yl]mercaptobutanoate Formula (I): $X_1=5$-Cl, $X_2=H$, $X_3=2$-F, $X_4=4$-Br, $A=2$-pyridine, $D=CO_2Et$, $B=S$, $R_1=R_2=R_3=R_4=H$, $n=2$
Crystals melting at 94° C.

EXAMPLE 22

Ethyl 2-[1-(4-chlorobenzyl)-5-chloroimidazo[4,5-b]pyridin-2-yl]mercapto 2-methylpropionate Formula (I): $X_1=5$-Cl, $X_2=H$, $X_3=4$-Cl, $X_4=H$, $A=2$-pyridine, $D=CO_2Et$, $B=S$, $R_1=R_2=CH_3$, $n=0$
Oil used as such for the next step.

EXAMPLE 23

Ethyl 4-[1-(4-chlorobenzyl)imidazo[4,5-b]pyridin-2-yl]mercaptobutanoate

Formula (I): $X_1=H$, $X_2=X_3=H$, $X_4=4$-Cl, $A=2$-pyridine, $D=CO_2Et$, $B=S$, $R_1=R_2=R_3=R_4=H$, $n=2$
Oil used as such for the next step.

EXAMPLE 24

Ethyl 4-(benzimidazol-2-yl)mercaptobutanoate

Formula (XI): $X_1=X_2=H$, $B=S$, $D=CO_2Et$, $R_1=R_2=R_3=R_4=H$, $n=2$ 50 g of 2-mercaptobenzimidazole are dissolved in 300 ml of ethanol, and a solution of 7.65 g of sodium in 150 ml of ethanol is added at room temperature, with stirring. The mixture is stirred for a few minutes at room temperature and 64.3 g of ethyl 4-bromobutyrate are added rapidly. The reaction mixture is refluxed for 6 hours and then cooled. The solvents are evaporated off to dryness under vacuum, the residue is taken up with water and the crystals obtained are filtered off, washed with water and then with ether and dried to give 85 g of ethyl 4-(benzimidazol-2-yl)mercaptobutanoate in the form of crystals melting at 70°–72° C.

EXAMPLE 25

Ethyl 5-(benzimidazol-2-yl)mercaptopentanoate

Formula (XI): $X_1=X_2=H$, $B=S$, $D=CO_2Et$, $R_1=R_2=R_3=R_4=H$, $n=3$
Prepared by the procedure of Example 24.
Crystals melting at 100° C.

EXAMPLE 26

Ethyl 4-[1-(4-chlorobenzyl)benzimidazol-2-yl]mercaptobutanoate

Formula (I): $X_1=H$, $X_2=X_3=H$, $X_4=4$-Cl, $A=$phenyl, $D=CO_2Et$, $B=S$, $R_1=R_2=R_3=R_4=H$, $n=2$ 20 g of ethyl 4-(benzimidazol-2-yl)mercaptobutanoate, prepared in Example 24, are added to a suspension of 2.9 g of 60% sodium hydride in 150 ml of anhydrous dimethylformamide. The mixture is stirred for 30 minutes at 80° C. and then cooled to room temperature and a solution of 12.7 g of 4-chloro-chloromethylbenzene in 20 ml of anhydrous dimethylformamide is added dropwise.

The mixture is refluxed for 5 hours and the solvent is evaporated off to dryness. The residue is taken up with water and extracted with ethyl acetate and the organic phase is dried and then evaporated under vacuum to give 27 g of ethyl 4-[1-(4-chlorobenzyl)benzimidazol-2-yl]mercaptobutanoate in the form of an oil, which is used as such for the next step. The following Example was prepared by the same procedure:

EXAMPLE 27

Ethyl 4-[1-(2,4-dichlorobenzyl)imidazol-2-yl]mercaptobutanoate

Formula (I): $X_1=H$, $X_2=H$, $X_3=2$-Cl, $X_4=4$-Cl, $A=$phenyl, $D=CO_2Et$, $B=S$, $R_1=R_2=R_3=R_4=H$, $n=2$
Crystals melting at 92° C.

EXAMPLE 28

Acid chloride ethyl ester of 3,3-dimethyglutaric acid

Formula (VIII): $R_5=R_6=H$, $R_1=R_2=CH$ , $R_3=R_4=H$, $n=1$, $D=CO_2Et$ 50 g of 3,3-di.methylglutaric anhydride are dissolved in 500 ml of absolute ethanol and the mixture is refluxed for 12 hours. The alcohol is evaporated off to dryness under vacuum, 250 ml of toluene are added to the residue and 45 ml of thionyl chloride are then added dropwise at room temperature, with stirring.

The mixture is heated at 80° C. for two hours, the solvents are then evaporated off and the residue is distilled at between 115° and 125° C. under 20 mm of mercury to give 58.2 g of the acid chloride ethyl ester of 3,3-dimethylglutaric acid.

The following Examples were prepared by the same procedure:

EXAMPLE 29

Acid chloride ethyl ester of 3-methylglutaric acid

Formula (VIII): $R_5=R_6=H$, $R_1=CH_3$, $R_2=R_3=R_4=H$, $n=1$, $D=CO_2Et$
Oil used as such for the next step.

EXAMPLE 30

Acid chloride ethyl ester of 3,3-diethylglutaric acid

Formula (VIII): $R_5=R_6=H$, $R_1=R_2=C_2H_5$, $R_3=R_4=H$, $n=1$, $D=CO_2Et$
Oil used as such for the next step.

EXAMPLE 31

Acid chloride ethyl ester of 3-methyl-3-ethylglutaric acid

Formula (VIII): $R_5=R_6=H$, $R_1=CH_3$, $R_2=C_2H_5$, $R_3=R_4=H$, $n=1$, $D=CO_2Et$
Oil used as such for the next step.

EXAMPLE 32

Acid chloride ethyl ester of cyclohexane-1,1,-diacetic acid

Formula (VIII): $R_5=R_6=H$, $R_1+R_2=CH_2-CH_2-CH_2-CH_2-CH_2$, $R_3=R_4=H$, $n=1$, $D=CO_2ET$
Oil boiling at 170°–175° C. under 25 mm of mercury.

EXAMPLE 33

Acid chloride ethyl ester of cyclopentane-1,1-diacetic acid

Formula (VIII): $R_5=R_6=H$, $R_1+R_2=CH_2-CH_2-CH_2-CH_2$, $R_3=R_4=H$, $n=1$, $D=CO_2Et$
Oil boiling at 165°–70° C. under 25 mm of mercury.

EXAMPLE 34

Ethyl 4-[1-(4-chlorobenzyl)-5-fluorobenzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=5$-F, $X_2=H$, $X_3=4$-Cl, $X_4=H$ 10 g of 2-(4-chlorobenzylamino)-5-fluoroaniline, prepared in Example 8, are dissolved in 100 ml of chloroform, stabilized with amylene, and 6 ml of triethylamine. A solution of 8.25 g of the acid chloride ethyl ester of 3,3-dimethylglutaric acid, prepared in Example 28, in 20 ml of chloroform, stabilized with amylene, is added dropwise. The mixture is stirred for two hours at room temperature, the crystals formed are filtered off and the solvents are evaporated off under vacuum. The residue obtained is dissolved in 200 ml of ethanol and 30 ml of concentrated hydrochloric acid and the mixture is refluxed for 10 hours. The solvents are evaporated off to dryness and the residue is taken up with water and then extracted with ethyl acetate. The organic phase is dried and evaporated under vacuum to give 14 g of ethyl 4-[1-(4-chlorobenzyl)-5-fluorobenzimidazol-2-yl]-3,3-dimethylbutanoate in the form of an oil, which is used as such for the next step.

The following Examples were synthesized by the same procedure:

EXAMPLE 35

Ethyl
[1-[1-(4-chlorobenzyl)-5-fluorobenzimidazol-2-yl]methylcyclopent-1-yl]acetate Formula (I): $R_1+R_2=CH_2-CH_2-CH_2-CH_2$, $R_3=R_4=H$, $n=1$, $D=CO_2Et$, $A=$phenyl, $B=CH_2$, $X_1=5\text{-}F$, $X_2=H$, $X_3=4\text{-}Cl$, $X_4=H$ Oil used as such for the next step.

EXAMPLE 36

Ethyl
[1-[1-(4-chlorobenzyl)-5-fluorobenzimidazol-2-yl]methylcyclohex-1-yl]acetate Formula (I): $R_1+R_2=CH_2-CH_2-CH_2-CH_2-CH_2$, $R_3=R_4=H$, $n=1$, $D=CO_2Et$, $A=$phenyl, $B=CH_2$, $X_1=5\text{-}F$, $X_2=H$, $X_3=4\text{-}Cl$, $X_4=H$ Oil used as such for the next step.

EXAMPLE 37

Ethyl
4-[1-(3,4-dichlorobenzyl)-5-fluorobenzimidazol-2-yl]-3,3-dimethylbutanoate Formula (I): $R_1=R_2=CH_2$, $R_3=R_4=H$, $n=1$, $D=CO_2Et$, $A=$phenyl, $B=CH_2$, $X_1=5\text{-}F$, $X_2=H$, $X_3=3\text{-}Cl$, $X_4=4\text{-}Cl$ Oil used as such for the next step.

EXAMPLE 38:

Ethyl 4-[1-(4-chlorobenzyl) 5 chlorobenzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=5\text{-}Cl$, $X_2=H$, $X_3=4\text{-}Cl$, $X_4=H$ Oil used as such for the next step.

EXAMPLE 39:

Ethyl
4-[1-(4-chlorobenzyl)-5-methoxybenzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_1=5\text{-}MeO$, $X_2=H$, $X_3=4\text{-}Cl$, $X_4=H$ Oil used as such for the next step.

EXAMPLE 40

Ethyl 4-(benzimidazol-2-yl)-3,3-dimethylbutanoate

Formula (XI): $B=CH_2$, $R_1=R_2=CH_3$, $R_3=R_4=H$, $n=1$, $D=CO_2Et$, $X_1=X_2=H$ A solution of 139.2 of the acid chloride ethyl ester of 3,3-dimethylglutaric acid, prepared in Example 28, in 125 ml of chloroform, stabilized with amylene, is added dropwise, at a temperature of between 5° C. and 10° C., to a solution of 72.8 g of orthophenylenediamine and 112 ml of triethylamine in 1 l of anhydrous tetrahydrofuran. The mixture is stirred at 0° C. for two hours and then at 50° C. for one hour; the crystals are filtered off and the solvents are evaporated off under vacuum. The residue is taken up in 4.4 l of ethanol and 444 ml of concentrated hydrochloric acid and the mixture is refluxed for 12 hours. The solvents are evaporated off and the residue is taken up with water and then neutralized with a 1 N solution of sodium hydroxide and extracted with ether. The ether phase is dried and then evaporated under vacuum to give 99 g of ethyl 4-(benzimidazol-2-yl)-3,3-dimethylbutanoate in the form of crystals melting at 123° C.

The following Examples were prepared by the same procedure:

EXAMPLE 41

Ethyl
4-(5,6-dichlorobenzimidazol-2-yl)-3,3-dimethylbutanoate

Formula (XI): $B=CH_2$, $R_1=R_2=CH_3$, $R_3=R_4=H$, $n=1$, $D=CO_2Et$, $X_1=5\text{-}Cl$, $X_2=6\text{-}Cl$ Crystals melting at 128° C.

EXAMPLE 42

Ethyl 4-(benzimidazol-2-yl)-3 methyl-3-ethylbutanoate

Formula (XI): $B=CH_2$, $R_1=CH_3$, $R_2=C_2H_5$, $R_3=R_4=H$, $n=1$, $D=CO_2Et$, $X_1=X_2=H$ Oil used as such for the next step.

EXAMPLE 43

Ethyl 4-(benzimidazol-2-yl)-3,3-diethylbutanoate

Formula (XI): $B=CH_2$, $R_1=R_2=C_2H_5$, $R_3=R_4=H$, $n=1$, $D=CO_2Et$, $X_1=X_2=H$ Crystals melting at 81° C.

EXAMPLE 44

Ethyl 4-(benzimidazol-2-yl)-3-methylbutanoate

Formula (XI): $B=CH_2$, $R_1=CH_3$, $R_2=R_3=R_4=H$, $n=1$, $D=CO_2Et$, $X_1=X_2=H$ Crystals melting at 105° C.

EXAMPLE 45

Ethyl
4-[1-(4-chlorobenzyl)benzimidazol-2-yl]-3,3-dimethylbutanoate

Formula (I): $R_1=R_2=CH_3$, $R_4=R_4=H$, $n=1$, $D=CO_2Et$, $A=$phenyl, $B=CH_2$, $X_1=H$, $X_2=X_3=H$, $X_4=4\text{-}Cl$ 9 g of ethyl 4-(benzimidazol-2-yl)-3,3-dimethylbutanoate, prepared in Example 40, are added to a suspension of 21.5 g of 60% sodium hydride in 50 ml of anhydrous dimethylformamide. The mixture is stirred for 1 hour at 50° C., 5.6 g of 4-chlorobenzyl chloride are then added and the solution obtained is heated for 5 hours at 90° C. The solvents are concentrated under vacuum and the residue is taken up with water and then extracted with ether. The ether phase is washed with water and then dried over magnesium sulfate and the ether is evaporated off to dryness to give 12.9 g of ethyl 4-[1-(4-chlorobenzyl)benzimidazol-2-yl]-3,3-dimethylbutanoate in the form of an oil, which is used as such for the next step.

The following Examples were prepared by the same procedure:

EXAMPLE 46

Ethyl
4-[1-(2-fluoro-4-bromobenzyl)benzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=H$, $X_2=H$, $X_3=2\text{-}F$, $X_4=4\text{-}Br$ Oil used as such for the next step.

EXAMPLE 47

Ethyl 4-(1-benzylbenzimidazol-2-yl)-3,3-dimethylbutanoate

Formula (I): $R_1=R_2=CH_3$, $R_3=R_4=H$, $n=1$, $D=CO_2Et$, $A=$phenyl, $B=CH_2$, $X_1=X_2=X_3=X_4=H$ Oil used as such for the next step.

EXAMPLE 48

Ethyl 4-[1-(4-methylbenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_1=X_2=X_3=H$, $X_4=4\text{-Me}$ Oil used as such for the next step.

EXAMPLE 49

Ethyl 4-[1-(4-fluorobenzyl)benzimidazol-2-yl]-3,3-dimethylbutanoate

Formula (I): $R_1=R_2=CH_3$, $R_3=R_4=H$, $n=1$, $D=CO_2Et$, $A=$phenyl, $B=CH_2$, $X_1=X_2=X_3=H$, $X_4=4\text{-F}$ Oil used as such for the next step.

EXAMPLE 50

Ethyl 4-[1-(4-methoxybenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_3=4\text{-MeO}$, $X_1=X_2=X_4=H$ Oil used as such for the next step.

EXAMPLE 51

Ethyl 4-[1-(4-bromobenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_3=4\text{-Br}$, $X_1=X_2=X_4=H$ Oil used as such for the next step.

EXAMPLE 52

Ethyl 4-[1-(4-chlorobenzyl)-5,6-dichlorobenzimidazol-2-yl]-3,3-dimethylbutanoate Formula (I): $R_1=R_2=CH_3$, $R_3=R_4=H$, $n=1$, $D=CO_2Et$, $B=CH_2$, $A=$phenyl, $X_3=5\text{-Cl}$, $X_2=6\text{-Cl}$, $X_3=4\text{-Cl}$, $X_4=H$ Oil used as such for the next step.

EXAMPLE 53

Ethyl 4-[1-(3-trifluoromethylbenzyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_1=H$, $X_2=X_3=H$, $X_4=3\text{-CF}$ Oil used as such for the next step.

EXAMPLE 54

Ethyl 4-[1-(4-chlorobenzyl)benzimidazol-2-yl]-3-methyl-3-ethylbutanoate

Formula (I): $R_1=CH_3$, $R_2=C_2H_5$, $R_3=R_4=H$, $n=1$, $D=CO_2Et$, $B=CH_2$, $A=$phenyl, $X_1=H$, $X_2=X_3=H$, $X_4=4\text{-Cl}$ Oil used as such for the next step.

EXAMPLE 55

Ethyl 4-[1-(4-chlorobenzyl)benzimidazol-2-yl]-3,3-diethylbutanoate

Formula (I): $R_1=R_2=C_2H_5$, $R_3=R_4=H$, $n=1$, $D=CO_2Et$, $B=CH_2$, $A=$phenyl, $X_1=H$, $X_2=H$, $X_3=4\text{-Cl}$, $X_4=H$ Oil used as such for the next step.

EXAMPLE 56

Ethyl 4-[1-(4-chlorobenzyl)benzimidazol-2-yl]-3-methylbutanoate

Formula (I): $R_1=CH_3$, $R_2=H$, $R_3=R_4=H$, $n=1$, $D=CO_2Et$, $B=CH_2$, $A=$phenyl, $X_1=X_2=X_3=H$, $X_4=4\text{-Cl}$ Oil used as such for the next step.

EXAMPLE 57

Ethyl 4-[1-(naphth-2-ylmethyl)benzimidazol-2-yl]-3,3-dimethylbutanoate

Formula (I): $R_1=R_2=CH_3$, $R_3=R_4=H$, $n=1$, $D=CO_2Et$, $B=CH_2$, $A=$phenyl, $X_3+X_4$ form a phenyl ring in the 3,4-position, $X_1=X_2=H$ Oil used as such for the next step.

EXAMPLE 58

4-(1 Benzylbenzimidazol-2-yl)-3,3-dimethylbutanoic acid

Formula (I): $R_1=R_2=CH_3$, $R_3=R_4=H$, $n=1$, $D=CO_2H$, $B=CH_2$, $A=$phenyl, $X_1=X_2=X_3=X_4=H$ 9 g of ethyl 4-(1-benzylbenzimidazol-2-yl)-3,3-dimethylbutanoate, prepared in Example 47, are dissolved in a mixture composed of 90 ml of concentrated hydrochloric acid, 270 ml of water and 250 ml of acetic acid. The mixture is refluxed for 4 hours and the solvents are concentrated under vacuum. The residue is taken up with a 1 N solution of sodium hydroxide and the resulting mixture is washed with ether; the aqueous phase is acidified by having sulfur dioxide bubbled through it until the pH is 5-6, and the crystals formed are filtered off and washed with water and isopropyl ether to give 5.3 g of 4-(1-benzylbenzimidazol-2-yl)-3,3-dimethylbutanoic acid in the form of crystals melting at 160°-1° C.

The following compounds were prepared by the same procedure:

EXAMPLE 59

5-[1-(4-Chlorobenzyl)-5-fluorobenzimidazol-2-yl]mercaptopentanoic acid

Formula (I): $R_1=R_2=R_3=R_4=H$, $n=3$, $D=CO_2H$, $B=S$, $A=$phenyl, $X_1=5\text{-F}$, $X_2=X_3=H$, $X_4=4\text{-Cl}$

EXAMPLE 60

4-[1-(2-Fluoro-4-bromobenzyl)-5-chloroimidazo[4,5-b]pyridin-2-yl]mercaptobutanoic acid Formula (I): $R_1=R_2=R_3=R_4=H$, n=2, $D=CO_2H$, B=S, A=pyridine, $X_1$=5-Cl, $X_2$=H, $X_3$=2-F, $X_4$=4-Br Crystals melting at 156°–158° C.

EXAMPLE 61

2-[1-(4-Chlorobenzyl)-5-chloroimidazo[4,5-b]pyridin-2-yl]mercapto-2-methylpropanoic acid Formula (I): $R_1=R_2=CH_3$, n=0, $D=CO_2H$, B=S, A=pyridine, $X_1$=5-Cl, $X_2$=H, $X_3$=4-Cl, $X_4$=H Crystals melting at 188°–189° C.

EXAMPLE 62

4-[1-(4-Chlorobenzyl)imidazo[4,5-b]pyridin-2-yl]mercaptobutanoic acid

Formula (I): $R_1=R_2=R_3=R_4=H$, n=2, $D=CO_2H$, B=S, A=pyridine, $X_1=X_2=H$, $X_3$=4-Cl, $X_4$=H Crystals melting at 121°–122° C.

EXAMPLE 63

4-[1-(4-Chlorobenzyl)benzimidazol-2-yl]mercaptobutanoic acid

Formula (I): $R_1=R_2=R_3=R_4=H$, n=2, $D=CO_2H$, =B=S, A=phenyl, $X_1=X_2=X_3=H$, $X_4$=4-Cl Crystals melting at 187°–190° C.

EXAMPLE 64

4-[1 (2,4-Dichlorobenzyl)benzimidazol-2-yl]mercaptobutanoic acid

Formula (I): $R_1=R_2=R_3=R_4=H$, n=2, $D=CO_2H$, B=S, A=phenyl, $X_1=X_2=H$, $X_3$=2-Cl, $X_4$=4-Cl Crystals melting at 117°–120° C.

EXAMPLE 65

4-[1-(4-Chlorobenzyl)-5 fluorobenzimidazol-2-yl]mercaptobutanoic acid

Formula (I): $R_1=R_2=R_3=R_4=H$, n=2, $D=CO_2H$, B=S, A=phenyl, $X_1$=5-F, $X_2=X_3=H$, $X_4$=4-Cl Crystals melting at 176°–178 C.

EXAMPLE 66

4-[1-(4-Methylbenzyl)benzimidazol-2-yl]-3,3-dimethylbutanoic acid

Formula (I): $R_1=R_2=CH_3$, $R_3=R_4=H$, n=1, $D=CO_2H$, $B=CH_2$, A=phenyl, $X_1=X_2=X_3=H$, $X_4$=4-Me Crystals melting at 147°–148° C.

EXAMPLE 67

4-(4-Fluorobenzyl)benzimidazol-2-yl]-3,3-dimethylbutanoic acid

Formula (I): $R_1=R_2=CH_3$, $R_3=R_4=H$, n=1, $D=CO_2H$, $B=CH_2$, A=phenyl, $X_1=X_2=X_3=H$, $X_4$=4-F Crystals melting at 180°–181° C.

EXAMPLE 68

4-[1-(4-Methoxybenzyl)benzimidazol-2-yl]-3,3-dimethybutanoic acid

Formula (I): $R_1=R_2=CH_3$, $R_3=R_4=H$, n=1, $D=CO_2H$, $B=CH_2$, A=phenyl, $X_1=X_2=X_3=H$, $X_4$=4-MeO Crystals melting at 149°–150° C.

EXAMPLE 69

4-[1-(4 Bromobenzyl)benzimidazol-2-yl]-3,3-dimethylbutanoic acid

Formula (I): $R_1=R_2=CH_3$, $R_3=R_4=H$, n=1, $D=CO_2H$, $B=CH_2$, A=phenyl, $X_1=X_2=X_3=H$, $X_4$=4-Br Crystals melting at 171°–172° C.

EXAMPLE 70

4-[1-(4-Chlorobenzyl)-5,6-dichlorobenzimidazol-2-yl]-3,3-dimethylbutanoic acid

Formula (I): $R_1=R_2=CH_3$, $R_3=R_4=H$, n=1, $D=CO_2H$, $B=CH_2$, A=phenyl, $X_1$=5-Cl, $X_2$=6-Cl, $X_3$=H, $X_4$=4-Cl Crystals melting at 197°–199° C.

EXAMPLE 71

4-[1-(3-Trifluoromethylbenzyl)benzimidazol-2-yl]-3,3-dimethylbutanoic acid

Formula (I): $R_1=R_2=CH_3$, $R_3=R_4=H$, n=1, $D=CO_2H$, $B=CH_2$, A=phenyl, $X_1=X_2=X_3=H$, $X_4$=3-CF.

Crystals melting at 163°–164° C.

EXAMPLE 72

[10[1-(4-Chlorobenzyl)-5-fluorobenzimidazol-2-yl]-methylcyclopent-1 yl]acetic acid Formula (I): $R_1+R_2=CH_2CH_2CH_2CH_2$, $R_3=R_4=H$, n=1, $D=CO_2H$, $B=CH_2$, A=phenyl, $X_1$=5-F, $X_2=X_3=H$, $X_4$=4-Cl Crystals melting at 164°–165° C.

EXAMPLE 73

[1-[1-(4-Chlorobenzyl)-5-fluorobenzimidazol-2-yl]methylcyclohex-1-yl]acetic acid Formula (I): $R_1+R_2=CH_2CH_2CH_2CH_2CH_2$, $R_3=R_4=H$, n=1, $D=CO_2H$, $B=CH_2$, A=phenyl, $X_1$=5-F, $X_2=X_3=H$, $X_4$=4-Cl Crystals melting at 182°–184° C.

EXAMPLE 74

4-[1-(4-Chlorobenzyl)-5-fluorobenzimidazol-2-yl]-3,3-dimethylbutanoic acid

Formula (I): $R_1=R_2=CH_3$, $R_3=R_4=H$, n=1, $D=CO_2H$, $B=CH_2$, A=phenyl, $X_1$=5-F, $X_2=X_3=H$, $X_4$=4-Cl Crystals melting at 164°–165° C.

EXAMPLE 75

4-[1-(4-Chlorobenzyl)benzimidazol-2-yl]-3-methyl-3-ethylbutanoic acid

Formula (I): $R_1=C_2H_5$, $R_2=CH_3$, $R_3=R_4=H$, n=1, $D=CO_2H$, $B=CH_2$, A=phenyl, $X_1=X_2=X_3=H$, $X_4$=4-Cl Crystals melting at 120°-123° C.

EXAMPLE 76

4-[1-(2-Fluoro-4-bromobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A$=phenyl, $X_1=X_2=H$, $X_3=2$-F, $X_4=4$-Br Crystals melting at 147°-148° C.

EXAMPLE 77

4-[1-(4-Chlorobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A$=phenyl, $X_1=X_2=X_3=H$, $X_4=4$-Cl Crystals melting at 170°-171° C.

EXAMPLE 78

4-[1-(4-Chlorobenzyl)-5-methoxybenzimidazol-2-yl]-3,3-dimethylbutanoic acid

Formula (I): $R_1=R_2=CH_3$, $R_3=R_4=H$, $n=1$, $D=CO_2H$, $B=CH_2$, $A$=phenyl, $X_1=5$-MeO, $X_2=X_3=H$, $X_4=4$-Cl Crystals melting at 174°-176° C.

EXAMPLE 79

4-[1(4-Chlorobenzyl)-5-chlorobenzimidazol-2-yl]-3,3-dimethylbutanoic acid

Formula (I): $R_1=R_2=CH_3$, $R_3=R_4=H$, $n=1$, $D=CO_2H$, $B=CH_2$, $A$=phenyl, $X_1=5$-Cl, $X_2=X_3=H$, $X_4=4$-Cl Crystals melting at 205°-207° C.

EXAMPLE 80

4-[1-(3,4-Dichlorobenzyl)-5-fluorobenzimidazol-2-yl]-3,3-dimethylbutanoic acid

Formula (I): $R_1=R_2=CH_3$, $R_3=R_4=H$, $n=1$, $D=CO_2H$, $B=CH_2$, $A$=phenyl, $X_1=5$-F, $X_2=H$, $X_3=3$-Cl, $X_4=4$-Cl Crystals melting at 177°-180° C.

EXAMPLE 81

4-[1-(4-Nitrobenzyl)benzimidazol-2-yl]-3,3-dimethylbutanoic acid

Formula (I): $R_1=R_2=CH_3$, $R_3=R_4=H$, $n=1$, $D=CO_2H$, $B=CH_2$, $A$=phenyl, $X_1=X_2=X_3=H$, $X_4=4$-$NO_2$ Crystals melting at 192°-194° C.

EXAMPLE 82

4-[1-(4-Chlorobenzyl)benzimidazol-2-yl]-3,3-diethylbutanoic acid

Formula (I): $R_1=R_2=C_2H_5$, $R_3=R_4=H$, $n=1$, $D=CO_2H$, $B=CH_2$, $A$=phenyl, $X_1=X_2=X_3=H$, $X_4=4$-Cl Crystals melting at 139°-140° C.

EXAMPLE 83

4-[1-(4-Chlorobenzyl)benzimidazol-2-yl]-3-methylbutanoic acid

Formula (I): $R_1=H$, $R_2=CH_3$, $R_3=R_4=H$, $n=1$, $D=CO_2H$, $B=CH_2$, $A$=phenyl, $X_1=X_2=X_3=H$, $X_4=4$-Cl Crystals melting at 201°-202° C.

EXAMPLE 84

4-[1-(Naphth-2-ylmethyl)benzimidazol-2-yl]-3,3-dimethylbutanoic acid

Formula (I): $A$=phenyl, $B=CH$, $D=CO_2H$, $R_1=R_2=CH_3$, $R_3=R_4=H$, $n=1$, $X_1=X_2=H$, $X_3+X_4$ form a phenyl ring in the 3,4-position Crystals melting at 147°-149° C.

EXAMPLE 85

4-[1-(4-Chlorobenzyl)benzimidazol-2-yl]-3,3-dimethylbutanamide

Formula (I): $R_1=R_2=CH_3$, $R_3=R_4=H$, $n=1$, $B=CH_2$, $D=CONH_2$, $A$=phenyl, $X_3=4$-Cl, $X_1=X_2=X_4=H$ 11.7 g of 4-[1-(4-chlorobenzyl)benzimidazol-2-yl]-3,3-dimethylbutanoic acid, prepared in Example 77, are added to 100 ml of anhydrous toluene and 3 ml of thionyl chloride. The mixture is heated at 80° C. for 4 hours and the solvents are evaporated off under vacuum. The residue is taken up in 50 ml of chloroform, stabilized with amylene, and added dropwise to 50 ml of 28% ammonium hydroxide. When the addition is complete, the mixture is stirred at room temperature for 1 hour 30 minutes and then decanted. The organic phase is dried over magnesium sulfate and the solvent is evaporated off to dryness under vacuum. The residue crystallizes from isopropyl ether and is recrystallized from acetonitrile to give 5.1 g of 4-[1-(4-chlorobenzyl)benzimidazol-2-yl]-3,3-dimethylbutanamide in the form of crystals melting at 163°-165° C.

EXAMPLE 86

4-[1-(4-Chlorobenzyl)benzimidazol-2-yl]-3,3-dimethylbutyronitrile

Formula (I): $R_1=R_2=CH_3$, $R_3=R_4=H$, $n=1$, $B=CH_2$, $D=CN$, $A$=phenyl, $X_3=4$-Cl, $X_1=X_2=X_4=H$ 2.7 g of 4-[1-(4-chlorobenzyl)benzimidazol-2-yl]-3,3-dimethylbutanamide are dissolved in 50 ml of chloroform. 2.3 ml of phosphorus oxychloride are added and the mixture is refluxed for 5 hours. After cooling, the solvents are evaporated off under vacuum and the residue is taken up with water and extracted with ethyl acetate. The organic phase is dried over magnesium sulfate and evaporated to dryness under vacuum to give an oil which crystallizes from ether. The crystals are filtered off, washed with ether and then dried to give 2.5 g of 4-[1-(4-chlorobenzyl)benzimidazol-2-yl]-3,3-dimethylbutyronitrile in the form of crystals melting at 110° C.

EXAMPLE 87

4-[1-(4-Hydroxybenzyl)benzimidazol-2-yl]-3,3-dimethylbutanoic acid

Formula (I): $R_1=R_2=CH_3$, $R_3=R_4=H$, $n=1$, $B=CH_2$, $D=CO_2H$, $A$=phenyl, $X_4=4$-OH, $X_1=X_2=X_3=H$ 2 g of 4-[1-(4-methoxybenzyl)benzimidazol-2-yl]-3,3-dimethylbutanoic acid, prepared in Example 68, are dissolved in 40 ml of acetic acid and 40 ml of 48% hydrobromic acid. The mixture is refluxed for 3 hours and the solvents are evaporated off under vacuum. The residue is taken up with a 1 N solution of sodium hydroxide so as to adjust the pH to 9-10, and the resulting aqueous phase is washed with ether and then acidified with sulfur dioxide to pH 5.5. The crystals obtained are filtered off, washed with water and then with ether and then chromatographed on silica gel in a 9:1 chloroform/methanol eluent to give 0.4 g of 4-[1-(4-hydroxybenzyl)benzimidazol-2-yl]-3,3-dimethylbutanoic acid in the form of crystals melting at 215°-216° C.

EXAMPLE 88

Acid chloride ethyl ester of trans-cyclobutane-1,2-dicarboxylic acid

Formula (VIII): $R_1+R_5=CH_2—CH_2$, $R_2=R_6=H$, $D=CO_2Et$, $n=0$ 14.2 g of ethyl trans-cyclobutane-1,2-dicarboxylate are dissolved in 100 ml of ethanol, and 2.8 g of sodium hydroxide pellets are added together with 30 ml of water. The mixture is refluxed for 1 hour and the solvents are evaporated off under vacuum. The residue is taken up with water and washed with ether. The aqueous phase is acidified with dilute hydrochloric acid and extracted with ether. The ether phase is dried over magnesium sulfate and evaporated under vacuum to give 7.5 g of the monoethyl ester of transcyclobutane-1,2-dicarboxylic acid. 6 ml of thionyl chloride and 50 ml of toluene are added to these 7.5 g and the mixture is refluxed for two hours. The solvents are evaporated off to dryness to give 9 g of the acid chloride ethyl ester of trans-cyclobutane-1,2-dicarboxylic acid in the form of an oil, which is used as such for the next step.

EXAMPLE 89

Ethyl trans-2-[1 (4-chlorobenzyl)-5-fluorobenzimidazol-2 yl]cyclobutane 1-carboxylate Formula (I): $B=CR_5R_6$, $R_1+R_5=CH_2CH_2$, $R_2=R_6=H$, $n=0$, $D=CO_2Et$, $A=$phenyl, $X_1=5$-F, $X_2=H$, X6hd 3=4-Cl, $X_4=H$
Prepared by the procedure of Example 34.
Oil used as such for the next step.

EXAMPLE 90

Trans-2-[1 (4-chlorobenzyl)-5-fluorobenzimidazol-2-yl]cyclobutane-1 carboxylic acid Formula (I): $B=CR_5R_6$, $R_1+R_5=CH_2CH_2$, $R_2=R_6=H$, $n=0$, $D=CO_2H$, $A=$phenyl, $X_1=5$-F, $X_2=H$, $X_3=4$-Cl, $X_4=H$
Prepared by the procedure of Example 58.
Crystals melting at 173°-175° C.

EXAMPLE 91

Ethyl 4-[1-(4-chlorophenylmethyl)-5-chloroimidazo[4,5-b]pyridin-2-yl]-3,3-dimethylbutanoate Formula (I): $R_1=R_2=CH_3$, $R_3=R_4=H$, $n=1$, $D=COOEt$, $A=2$-pyridine, $B=CH_2$, $X_1=5$-Cl, $X_2=X_3=H$, $X_4=4$-Cl 16.5 g of 2-(4-chlorobenzylamino)-3-amino-5-chloropyridine, prepared in Example 14, are dissolved in a mixture consisting of 25 ml of ethanol and 25 ml of acetic acid. 12.1 g of ethyl 4-formyl-3,3-dimethylbutanoate are added and the mixture is stirred for 4 hours at room temperature. The solvents are evaporated off to dryness under vacuum and the residue is dissolved in 200 ml of 1,2-dimethoxyethane. 20 g of iodine are added and the solution is heated for 16 hours at 50° C. The solvent is then evaporated off to dryness under vacuum and the residue is taken up with water and extracted with ether. The ether phase is washed with water, dried over magnesium sulfate and evaporated. The oil obtained is chromatographed on silica gel in a 7:3 cyclohexane/ethyl acetate eluent to give 10 g of ethyl 4-[1-(4-chlorophenylmethyl)-5-chloroimidazo[4,5-b]pyridin-2-yl]-3,3-dimethylbutanoate in the form of an oil, which is used as such for the next step.

Preparation of ethyl 4-formyl-3,3-dimethylbutanoate:

40 g of the acid chloride ethyl ester of 3,3-dimethylglutaric acid, prepared in Example 28, are dissolved in 400 ml of tetrahydrofuran. 2 of 5% palladium-on-charcoal and 22.8 ml of 2,6-lutidine are added and the mixture is hydrogenated at normal pressure and room temperature. When the absorption of hydrogen has ceased, the catalyst is filtered off and the solvent is evaporated off under vacuum. The residue is taken up with water and extracted with ether. The ether phase is washed with a dilute solution of hydrochloric acid in the cold, washed with a solution of sodium bicarbonate in the cold, dried over magnesium sulfate and evaporated under vacuum to give, after distillation of the residue, 18 g of ethyl 4-formyl-3,3-dimethylbutanoate in the form of a liquid with a boiling point b.p.[20] of 112°-118° C.

EXAMPLE 92

4-[1-(4-Chlorophenylmethyl)-5-chloroimidazo[4,5-b]-pyridin-2 yl]3,3-dimethylbutanoic acid Formula (I): $R_1=R_2=CH_3$, $R_3=R_4=H$, $n=1$, $D=COOH$, $A=2$-pyridine, $B=CH_2$, $X_1=5$-Cl, $X_2=X_3=H$, $X_4=4$-Cl If the procedure of Example 58 is followed, except that ethyl 4-[1-(4-chlorophenylmethyl)-5-chloroimidazo[4,5-b]pyridin-2-yl]-3,3-dimethylbutanoate, prepared in Example 91, is used as the starting material, 4-[1-(4-chlorophenylmethyl)-5-chloroimidazo[4,5-b]pyridin-2-yl]-3,3-dimethylbutanoic acid is obtained in the form of crystals melting at 120°-122° C.

EXAMPLE 93

2-(4-Methylthiobenzyl)amino-5-fluoronitrobenzene

Formula (V): $X_1=5$-F, $X_2=X_3=H$, $X_4=4$-SCH$_3$, $A=$-phenyl 24.8 g of 2-amino-5-fluoronitrobenzene and 27.6 g of 4-methylthiobenzyl chloride are mixed and 14.4 g of anhydrous sodium acetate and 0.3 g of iodine are added. The mixture is heated at 120° C. for 12 hours, with stirring, and is then cooled, taken up with a dilute solution of hydrochloric acid and extracted with ethyl acetate. The organic phase is washed with dilute hydrochloric acid and then with water, dried over magnesium sulfate and evaporated to dryness. The oil obtained crystallizes from isopropyl ether to give 23.8 g of 2-(4-methylthiobenzyl)amino-5-fluoronitrobenzene in the form of crystals melting at 117° C.

EXAMPLE 94

2-(4-Methylthiobenzyl)amino-5-fluoroaniline

Formula (IV): $X_1=5\text{-}F$, $X_2=X_3=H$, $X_4=4\text{-}SCH_3$, $A=\text{phenyl}$
Prepared by the procedure of Example 8.
Crystals melting at 112° C.

EXAMPLE 95

Ethyl 4-[1-(4-methylthiobenzyl)-5-fluorobenzimidazol-2-yl]-3,3-dimethylbutanoate Formula (I): $R_1=R_2=CH_3$, $R_3=R_4=H$, $n=1$, $D=CO_2Et$, $A=\text{phenyl}$, $B=CH_2$, $X_1=5\text{-}F$, $X_2=X_3=H$, $X_4=4\ SCH_3$
Prepared by the procedure of Example 34.
Oil used as such for the next step.

EXAMPLE 96

4-[1-(4-Methylthiobenzyl)-5-fluorobenzimidazol-2-yl]-3,3-dimethylbutanoic acid

Formula (I): $R_1=R_2=CH_3$, $R_3=R_4=H$, $n=1$, $D=CO_2H$, $A=\text{phenyl}$, $B=CH_2$, $X_1=5\text{-}F$, $X_2=X_3=H$, $X_4=4\text{-}SCH_3$
Prepared by the procedure of Example 58.
Crystals melting at 154°–155° C.

EXAMPLE 97

4-[1-(4-Methylsulfonylbenzyl)-5-fluorobenzimidazol-2-yl]-3,3-dimethylbutanoic acid Formula (I): $R_1=R_2=CH_2$, $R_3=R_4=H$, $n=1$, $D=CO_2H$, $A=\text{phenyl}$, $B=CH_2$, $X_1=5\text{-}F$, $X_2=X_3=H$, $X_4=4\text{-}SO\ CH_3$ 3 g of 4-[1-(4-methylthiobenzyl)-5-fluorobenzimidazol-2-yl]-3,3-dimethylbutanoic acid, prepared in Example 96, are dissolved in 100 ml of methanol. The mixture is cooled to 0.C and 3.8 g of 70% meta-chloroperbenzoic acid are added. When the addition is complete, the mixture is stirred at room temperature for 10 hours. The crystals formed are filtered off, washed with methanol and then dried to give 2.4 g of 4-[1-(4-methylsulfonylbenzyl)-5-fluorobenzimidazol-2-yl]-3,3-dimethylbutanoic acid in the form of crystals melting at 221°–222° C.

EXAMPLE 98

2-(3,4-Dichlorobenzyl)amino-5-chloronitrobenzene

Formula (V): $X_1=5\text{-}Cl$, $X_2=H$, $X_3=3\text{-}Cl$, $X_4=4\text{-}Cl$, $A=\text{phenyl}$
Prepared by the procedure of Example 3.
Crystals melting at 129° C.

EXAMPLE 99

2-(3,4-Dichlorobenzyl)amino-5-chloroaniline

Formula (IV): $X_1=5\text{-}Cl$, $X_=H$, $X_3=3\text{-}Cl$, $X_4=4\text{-}Cl$, $A=\text{phenyl}$
Prepared by the procedure of Example 8.
Crystals melting at 80° C.

EXAMPLE 100

Ethyl 4-[1-(3,4-dichlorobenzyl)-5-chlorobenzimidazol-2-yl]-3,3-dimethylbutanoate Formula (I): $R_1=R_2=CH_3$, $R_3=R_4=H$, $n=1$, $D=CO_2Et$, $A=\text{phenyl}$, $B=CH_2$, $X_1=5\text{-}Cl$, $X_2=H$, $X_3=3\text{-}Cl$, $X_4=4\text{-}Cl$
Prepared by the procedure of Example 34.
Oil used as such for the next step.

EXAMPLE 101

4-[1-(3,4-Dichlorobenzyl)-5-chlorobenzimidazol-2-yl]-3,3-dimethylbutanoic acid

Formula (I): $R_1=R_2=CH_3$, $R_3=R_4=H$, $n=1$, $D=CO_2H$, $A=\text{phenyl}$, $B=CH_2$, $X_1=5\text{-}Cl$, $X_2=H$, $X_3=4\text{-}Cl$, $X_5=3\text{-}Cl$
Prepared by the procedure of Example 58.
Crystals melting at 183°–184° C.

EXAMPLE 102

2-(2-Fluoro-4-bromobenzyl)amino-5-fluoronitrobenzene

Formula (V): $X_1=5\text{-}F$, $X_2=H$, $X_3=2\text{-}F$, $X_4=4\text{-}Br$, $A=\text{phenyl}$
Prepared by the procedure of Example 1.
Crystals melting at 130° C.

EXAMPLE 103

2-(2-Fluoro-4-bromobenzyl)amino-5-fluoroaniline

Formula (IV): $X_1=5\text{-}F$, $X_2=H$, $X_3=2\text{-}F$, $X_4=4\text{-}Br$, $A=\text{phenyl}$
Prepared by the procedure of Example 8.
Oil used as such for the next step.

EXAMPLE 104

Ethyl 4-[I-(2-fluoro-4-bromobenzyl)-5-fluorobenzimidazol-2-yl]-3,3-dimethylbutanoate Formula (I): $R_1=R_2=CH_3$, $R_3=R_4=H$, $n=1$, $D=CO_2Et$, $A=\text{phenyl}$, $B=CH_2$, $X_1=5\text{-}F$, $X_2=H$, $X_3=2\text{-}F$, $X_4=4\text{-}Br$
Prepared by the procedure of Example 34.
Oil used as such for the next step.

EXAMPLE 105

4-[1-(2-Fluoro-4-bromobenzyl)-5-fluorobenzimidazol-2-yl]-3,3-dimethylbutanoic acid Formula (I): $R_1=R_2=CH_3$, $R_3=R_4=H$, $n=1$, $D=CO_2H$, $A=\text{phenyl}$, $B=CH_2$, $X_1=5\text{-}F$, $X_2=H$, $X_3=2\text{-}F$, $X_4=4\text{-}Br$
Prepared by the procedure of Example 58.
Crystals melting at 145°–7° C.

EXAMPLE 106

2-(4-Bromobenzyl)amino-5-fluoronitrobenzene

Formula (V): $X_1=5\text{-}F$, $X_2=H$, $X_3=4\text{-}Br$, $X_4=H$, $A=\text{phenyl}$
Prepared by the procedure of Example 1.
Crystals melting at 163° C.

EXAMPLE 107

2-(4-Bromobenzyl)amino-5-fluoroaniline

Formula (IV): $X_1=5$-F, $X_2=$H, $X_3=4$-Br, $X_4=$H, A=phenyl
Prepared by the procedure of Example 8.
Crystals melting at 97° C.

EXAMPLE 108

Ethyl 4-[1-(4-bromobenzyl)-5-fluorobenzimidazol-2-yl]3,3-dimethylbutanoate

Formula (I): $R_1=R_2=CH_3$, $R_3=R_4=$H, $n=1$, $D=CO_2Et$, A=phenyl, $B=CH_2$, $X_1=5$-F, $X_2=X_3=$H, $X_4=4$-Br
Prepared by the procedure of Example 34.
Oil used as such for the next step.

EXAMPLE 109

4-[1-(4-Bromobenzyl)-5-fluorobenzimidazol-2-yl]-3,3-dimethylbutanoic acid

Formula (I): $R_1=R_2=CH_3$, $R_3=R_4=$H, $n=1$, $D=CO_2H$, A=phenyl, $B=CH_2$, $X_1=5$-F, $X_2=X_3=$H, $X_4=4$-Br
Prepared by the procedure of Example 58.
Crystals melting at 172°–174° C.

EXAMPLE 110

2-(4-Methoxybenzyl)amino-5-chloronitrobenzene

Formula (V): $X_1=5$-Cl, $X_2=X_3=$H, $X_4=4$-OCH$_3$, A=phenyl
Prepared by the procedure of Example 3.
Crystals melting at 114° C.

EXAMPLE 111

2-(4-Methoxybenzyl)amino-5-chloroaniline

Formula (IV): $X_1=5$-Cl, $X_2=X_3=$H, $X_4=4$-OCH$_2$, A=phenyl
Prepared by the procedure of Example 8.
Crystals melting at 108° C.

EXAMPLE 112

Ethyl 4-[1-(4-methoxybenzyl)-5-chlorobenzimidazol-2-yl]-3,3-dimethylbutanoate

Formula (I): $R_1=R_2=CH_3$, $R_3=R_4=$H, $n=1$, $D=CO_2Et$, A=phenyl, $B=CH_2$, $X_1=5$-Cl, $X_2=X_3=$H, $X_4=4$-OCH.
Prepared by the procedure of Example 34.
Oil used as such for the next step.

EXAMPLE 113

4-[1-(4-Methoxybenzyl)-5-chlorobenzimidazol-2-yl]-3,3-dimethylbutanoic acid

Formula (I): $R_1=R_2=CH_3$, $R_3=R_4=$H, $n=1$, $D=CO_2H$, A=phenyl, $B=CH_2$, $X_1=5$-Cl, $X_2=X_3=$H, $X_4=4$-OCH
Prepared by the procedure of Example 58.
Crystals melting at 144°–145° C.

EXAMPLE 114

4-(4-Methylthiobenzyl)amino-5-chloronitrobenzene

Formula (V): $X_1=5$-Cl, $X_2=X_3=$H, $X_4=4$-SCH$_3$, A=p phenyl
Prepared by the procedure of Example 93.
Crystals melting at 74° C.

EXAMPLE 115

2-(4-Methylthiobenzyl)amino-5-chloroaniline

Formula (IV): $X_1=5$-Cl, $X_2=X_3=$H, $X_4=4$-SCH$_3$, A=phenyl
Prepared by the procedure of Example 8.
Crystals melting at 131° C.

EXAMPLE 116

Ethyl 4-[1-(4-methylthiobenzyl)-5-chlorobenzimidazol-2-yl]-3,3-dimethylbutanoate Formula (I): $R_1=R_2=CH_3$, $R_3=R_4=$H, $n=1$, $D=CO_2Et$, A=phenyl, $B=CH_2$, $X_1=5$-Cl, $X_2=X_3=$H, $X_4=4$-SCH.
Prepared by the procedure of Example 34.
Oil used as such for the next step.

EXAMPLE 117

4-[1-(4-Methylthiobenzyl)-5-chlorobenzimidazol-2-yl]-3,3-dimethylbutanoic acid

Formula (I): $R_1=R_2=CH_3$, $R_3=R_4=$H, $n=1$, $D=CO_2H$, A=phenyl, $B=CH_2$, $X_1=5$-Cl, $X_2=X_3=$H, $X_4=4$-SCH$_3$
Prepared by the procedure of Example 58.
Crystals melting at 138°–139° C.

EXAMPLE 118

4-[1-(4-Methylsulfoxybenzyl)-5-chlorobenzimidazol-2-yl]-3,3-dimethylbutanoic acid Formula (I): $R_1=R_2=CH_3$, $R_3=R_4=$H, $n=1$, $D=CO_2H$, A=phenyl, $B=CH_2$, $X_1=5$-Cl, $X_2=X_3=$H, X=4-SOCH$_3$ 5 g of 4-[1-(4-methylthiobenzyl)-5-chlorobenzimidazol-2-yl]-3,3-dimethylbutanoic acid, prepared in Example 117, are dissolved in 350 ml of methanol. The solution is stirred at 0 C and 2.9 g of 75% meta-chloroperbenzoic acid are then added. The mixture is stirred in the cold for 30 minutes and then at room temperature for 4 hours. The solution is concentrated to dryness, the residue is taken up with water and ether and the crystals formed are filtered off, washed with ether and then chromatographed on silica gel in a 90:10:0.5 ether/methanol/acetic acid eluent to give 2.5 g of 4-[1-(4-methylsulfoxybenzyl)-5-chlorobenzimidazol-2-yl]-3,3-dimethylbutanoic acid in the form of crystals melting at 161°–2° C.

EXAMPLE 119

4-[1-(4-Methylsulfonylbenzyl)-5-chlorobenzimidazol-2-yl]-3,3-dimethylbutanoic acid Formula (I): $R_1=R_2=CH_3$, $R_3=R_4=$H, $n=1$, $D=CO_2H$, A=phenyl, $B=CH_2$, $X_1=5$-Cl, $X_2=X_3=$H, $X_4=4$-SO$_2$CH$_3$
Prepared by the procedure of Example 97.
Crystals melting at 228°–30° C.

EXAMPLE 120

2-(2-Fluoro-4-chlorobenzyl)amino-5-chloronitrobenzene

Formula (V): $X_1=5$-Cl, $X_2=$H, $X_3=2$-F, $X_4=4$-Cl, A=phenyl
Prepared by the procedure of Example 3.

Crystals melting at 130° C.

EXAMPLE 121

2-(2-Fluoro-4-chlorobenzyl)amino-5-chloroaniline

Formula (IV): $X_1=5$-Cl, $X_2=$H, $X_3=2$-F, $X_4=4$-Cl, A=phenyl
Prepared by the procedure of Example 8.
Oil used as such for the next step.

EXAMPLE 122

Ethyl 4-[1-(2-fluoro-4-chlorobenzyl)-5-chlorobenzimidazol-2-yl]-3,3-dimethylbutanoate Formula (I): $R_1=R_2=CH_3$, $R_3=R_4=H$, $n=1$, $D=CO_2Et$, A=phenyl, $B=CH_2$, $X_1=5$-Cl, $X_2=$H, $X_3=2$-F, $X_4=4$-Cl
Prepared by the procedure of Example 34.
Oil used as such for the next step.

EXAMPLE 123

4-[1-(2-Fluoro-4-chlorobenzyl)-5-chlorobenzimidazol-2-yl]3,3-dimethylbutanoic acid Formula (I): $R_1=R_2=CH_3$, $R_3=R_4=H$, $n=1$, $D=CO_2H$, $B=CH_2$, $X_1=5$-Cl, $X_2=$H, $X_3=2F$, $X_4=4$-Cl
Prepared by the procedure of Example 58.
Crystals melting at 186°–188° C.

EXAMPLE 124

2-(4-Chlorobenzyl)amino-5-bromonitrobenzene

Formula (V): $X_1=5$-Br, $X_2=X_3=$H, $X_4=4$-Cl, A=phenyl
Prepared by the procedure of Example 3.
Crystals melting at 118° C.

EXAMPLE 125

2-(4-Chlorobenzyl)amino-5-bromoaniline

Formula (IV): $X_1=5$-Br, $X_2=X_3=$H, $X_4=4$-Cl, A=phenyl
Prepared by the procedure of Example 8.
Crystals melting at 149° C.

EXAMPLE 126

Ethyl 4-[1-(4-chlorobenzyl)-5-bromobenzimidazol-2-yl]-3,3-dimethylbutanoate

Formula (I): $R_1=R_2=CH_3$, $R_3=R_4=H$, $n=1$, $D=CO_2Et$, A=phenyl, $B=CH_2$, $X_1=5$-Br, $X_2=X_3=$H, $X_4=4$-Cl
Prepared by the procedure of Example 34.
Oil used as such for the next step.

EXAMPLE 127

4-[1 (4-Chlorobenzyl)-5-bromobenzimidazol-2-yl]-3,3-dimethylbutanoic acid

Formula (I): $R_1=R_2=CH_3$, $R_3=R_4=H$, $n=1$, $D=CO_2H$, A=phenyl, $B=CH_2$, $X_1=5$-Br, $X_2=X_3=$H, $X_4=4$-Cl
Prepared by the procedure of Example 58.
Crystals melting at 219°–221 C.

EXAMPLE 128

2-(4-Methoxybenzyl)amino-5-fluoronitrobenzene

Formula (V): $X_1=5$-F, $X_2=X_3=$H, $X_4=4$-OMe, A=phenyl
Prepared by the procedure of Example 1.
Crystals melting at 106° C.

EXAMPLE 129

2-(4-Methoxybenzyl)amino-5-fluoroaniline

Formula (IV): $X_1=5$-F, $X_2=X_3=$H, $X_4=4$-OMe, A=phenyl
Prepared by the procedure of Example 8.
Crystals melting at 123° C.

EXAMPLE 130

Ethyl 4-[1-(4-methoxybenzyl)-5-fluorobenzimidazol-2-yl]-3,3-dimethylbutanoate

Formula (I): $R_1=R_2=CH_3$, $R_3=R_4=H$, $n=1$, $D=CO_2Et$, A=phenyl, $X_1=5$-F, $X_2=X_3=$H, $X_4=4$-OMe
Prepared by the procedure of Example 34.
Oil used as such for the next step.

EXAMPLE 131

4-[1-(4-Methoxybenzyl)-5 fluorobenzimidazol-2-yl]-3,3-dimethylbutanoic acid

Formula (I): $R_1=R_2=CH_3$, $R_3$32 $R_4=H$, $n=1$, $D=CO_2H$, A=phenyl, $B=CH_2$, $X_1=5$-F, $X_2=X_3=$H, X6hd 4=4-OMe
Prepared by the procedure of Example 58.
Crystals melting at 137°–138° C.

EXAMPLE 132

2-(2-Fluoro-4-bromobenzyl)amino-5-chloronitrobenzene

Formula (V): $X_1=5$-Cl, X6hd 2=H, $X_3=2$-F, $X_4=4$-Br, A=phenyl
Prepared by the procedure of Example 3.
Crystals melting at 130° C.

EXAMPLE 133

2-(2-Fluoro-4-bromobenzyl)amino-5-chloroaniline

Formula (IV): $X_1=5$-Cl, $X_2=$H, $X_3=2$-F, $X_4=4$-Br, A=phenyl
Prepared by the procedure of Example 8.
Crystals melting at 89° C.

EXAMPLE 134

Ethyl 4-[1-(2-fluoro-4-bromobenzyl)-5-chlorobenzimidazol-2-yl]-3,3-dimethylbutanoate Formula (I): $R_1=R_2=CH_3$, $R_3=R_4=H$, $n=1$, $D=CO_2Et$, A=phenyl, $B=CH_2$, $X_1=5$-Cl, $X_2=$H, $X_3=2$-F, $X_4=4$-Br
Prepared by the procedure of Example 34.
Oil used as such for the next step.

EXAMPLE 135

4-[1-(2-Fluoro-4-bromobenzyl)-5-chlorobenzimidazol-2-yl]3,3-dimethylbutanoic acid Formula (I): $R_1=R_2=CH_3$, $R_3=R_4=H$, $n=1$, $D=CO_2H$, $A=$ phenyl, $B=CH_2$, $X_1=5$-Cl, $X_2=H$, $X_3=2$-F, $X_4=4$-Br
Prepared by the procedure of Example 58.
Crystals melting at 176°–7° C.

EXAMPLE 136

2-(4-Bromobenzyl)amino-5-chloronitrobenzene

Formula (V): $X_1=5$-Cl, $X_2=X_3=H$, $X_4=4$-Br, $A=$ phenyl
Prepared by the procedure of Example 3.
Crystals melting at 136° C.

EXAMPLE 137

2-(4-Bromobenzyl)amino-5-chloroaniline

Formula (IV): $X_1=5$-Cl, $X_2=X_3=H$, $X_4=4$-Br, $A=$ phenyl
Prepared by the procedure of Example 8.
Crystals melting at 152° C.

EXAMPLE 138

Ethyl 4-[1-(4-bromobenzyl)-5-chlorobenzimidazol-2-yl]-3,3-dimethylbutanoate

Formula (I): $R_1=R_2=CH_3$, $R_3=R_4=H$, $n=1$, $D=CO_2Et$, $A=$ phenyl, $B=CH_2$, $X_1=5$-Cl, $X_2=X_3=H$, $X_4=4$-Br
Prepared by the procedure of Example 34.
Oil used as such for the next step.

EXAMPLE 139

4-[1 (4-Bromobenzyl)-5-chlorobenzimidazol-2-yl]-3,3-dimethylbutanoic acid

Formula (I): $R_1=R_2=CH_3$, $R_3=R_4=H$, $n=1$, $D=CO_2H$, $A=$ phenyl, $B=CH_2$, $X_1=5$-Cl, $X_2=X_2=H$, $X_4=4$-Br
Prepared by the procedure of Example 34.
Oil used as such for the next step.

EXAMPLE 140

2-(Naphth-2-ylmethyl)amino-5-chloronitrobenzene

Formula (V): $X_1=5$-Cl, $X_2=H$, $A=$ phenyl, $X_3+X_4$ form a phenyl ring in the 3,4-position
Prepared by the procedure of Example 93.
Crystals melting at 143° C.

EXAMPLE 141

2(Naphth-2-ylmethyl)amino-5-chloroaniline

Formula (IV): $X_1=5$-Cl, $X_2=H$, $A=$ phenyl, $X_3+X_4$ form a phenyl ring in the 3,4-position
Prepared by the procedure of Example 8.
Crystals melting at 124° C.

EXAMPLE 142

Ethyl 4-[1-(naphth-2-ylmethyl)-5-chlorobenzimidazol-2-yl]-3,3-dimethylbutanoate

Formula (I): $R_1=R_2=CH_3$, $R_3=R_4=H$, $n=1$, $D=CO_2Et$, $A=$ phenyl, $B=CH_2$, $X_1=5$-Cl, $X_2=H$, and form a phenyl ring in the 3,4-position
Prepared by the procedure of Example 34.
Oil used as such for the next step.

EXAMPLE 143

4-[1-(Naphth-2-ylmethyl)-5-chlorobenzimidazol-2-yl]-3,3-dimethylbutanoic acid

Formula (I): $R_1=R_2=CH_3$, $R_3=R_4=H$, $n=1$, $D=CO_2H$, $A=$ phenyl, $B=CH_2$, $X_1=5$-Cl, $X_2=H$, X and form a phenyl ring in the 3,4-position
Prepared by the procedure of Example 58.
Crystals melting at 168°–169° C.

EXAMPLE 144

1-Naphth-2-ylmethyl)amino-5-fluoronitrobenzene

Formula (v): $X_1=5$-F, $X_2=H$, $A=$ phenyl, $X_3$ and $X_4$ form a phenyl ring in the 3,4-position
Prepared by the procedure of Example 93.
Crystals melting at 170° C.

EXAMPLE 145

1-(Naphth-2-ylmethyl)amino-5-fluoroaniline

Formula (IV): $X_1=5$-F, $X_2=H$, $A=$ phenyl, $X_3$ and $X_4$ form a phenyl ring in the 3,4-position
Prepared by the procedure of Example 8.
Crystals melting at 118° C.

EXAMPLE 146

Ethyl 4-[1-(naphth-2-ylmethyl)-5-fluorobenzimidazol-2-yl]-3,3-dimethylbutanoate

Formula (I): $R_1=R_2=CH_3$, $R_3=R_4=H$, $n=1$, $D=CO_2Et$, $A=$ phenyl, $B=CH_2$, $X_1=5$-F, $X_2=H$, $X_3$ and $X_4$ form a phenyl ring in the 3,4-position
Prepared by the procedure of Example 34.
Oil used as such for the next step.

EXAMPLE 147

4-[1(Naphth-2-ylmethyl)-5-fluorobenzimidazol-2-yl]-3,3-dimethylbutanoic acid

Formula (I): $R_1=R_2=CH_3$, $R_3=R_4=H$, $n=1$, $D=CO_2H$, $A=$ phenyl, $B=CH_2$, $X_1=5$-F, $X_2=H$, $X_3$ and $X_4$ and form a phenyl ring in the 3,4-position
Prepared by the procedure of Example 58.
Crystals melting at 157°–158° C.

EXAMPLE 148

Acid chloride ethyl ester of cyclopropane-1,1-diacetic acid

Formula (VIII): $R_5=R_6=H$, $R_1+R_2=CH_2CH_2$, $R_3=R_4=H$, $n=1$, $D=CO_2Et$
Prepared by the procedure of Example 28 from cyclopropane-1,1-diacetic anhydride.
Oil used as such for the next step.
Preparation of cyclopropane-1,1-diacetic anhydride:
11 g of cyclopropane-1,1-diacetonitrile (the preparation of which can be found in the references: SEYDEN; PENNE J.; ROUX; SCHMITT M. C.; Bull. Soc. Chim.

Fr. 1968, 9, 3810–3812, and CHAMBOUX B.; ETIENNE Y.; PALLAUD R.; C.R. Acad. Science Paris 1962, 255, p. 536–538) are added to 150 ml of 20% potassium hydroxide solution and the mixture is refluxed for 12 hours. After cooling, the mixture is washed with ether and the aqueous phase is acidified with hydrochloric acid and then saturated with sodium chloride and extracted with ethyl acetate. The organic phase is dried over magnesium sulfate and then evaporated to dryness to give 10.5 g of cyclopentane-1,1-diacetic acid melting at 105° C. This acid is dissolved in 50 ml of acetic anhydride and the mixture is refluxed for 5 hours. The solvent is evaporated off to dryness to give 10.2 g of cyclopropane-1,1-diacetic anhydride melting at 102° C.

EXAMPLE 149

Ethyl [1-[1-(4 chlorobenzyl)-5-fluorobenzimidazol-2-yl]methylcycloprop-1-yl]acetate Formula (I): $R_1+R_2=CH_2CH_2$, $R_3=R_4=H$, $n=1$, $D=CO_2Et$, $A=$phenyl, $B=CH_2$, $X_1=5$-F, $X_2=X_3=H$, $X_4=4$-Cl Prepared by the procedure of Example 34 from the acid chloride ester of cyclopropane-1,1-diacetic acid prepared in Example 148.

Oil used as such for the next step.

EXAMPLE 150

[1-[1-(4-Chlorobenzyl)-5-fluorobenzimidazol-2-yl]methylcycloprop-1-yl]acetic acid Formula (I): $R_1+R_2=CH_2CH_2$, $R_3=R_4=H$, $n=1$, $D=CO_2H$, $B=CH_2$, $A=$phenyl, $X_1=5$-F, $X_2=X_3=H$, $X_4=4$-Cl Prepared by the procedure of Example 58.

Crystals melting at 181°–3° C.

EXAMPLE 151

Acid chloride ethyl ester of trans-cyclopentane-1,2-dicarboxylic acid

Formula (VIII): $R_1+R_5=CH_2CH_2CH_2$, $R_2=R_6=H$, $D=CO_2Et$, $n=0$

Prepared by the procedure of Example 88.

Oil used as such for the next step.

EXAMPLE 152

Ethyl trans-2-[1-(4-chlorobenzyl)-5-fluorobenzimidazol--yl]cyclopentane-1-carboxylate Formula (I): $B=CR_5R_6$, $R_1+R_5=CH_2CH_2CH_2$, $R_2=R_6=H$, $n=0$, $D=CO_2Et$, $A=$phenyl, $X_1=5$-F, $X_2=H$, $X_3=4$-Cl, $X_4=H$ Prepared by the procedure of Example 34 from the acid chloride ethyl ester of trans-cyclopentane-1,2-dicarboxylic acid prepared in Example 151.

Oil used as such for the next step.

EXAMPLE 153

Trans 2-[1-(4-chlorobenzyl)-5-fluorobenzimidazol-2-yl]cyclopentane-1-carboxylic acid Formula (I): $B=CR_5R_6$, $R_1+R_5=CH_2CH_2CH_2$, $R_2=R_6=H$, $n=0$, $D=CO_2H$, $A=$phenyl, $X_1=5$-F, $X_2=H$, $X_3=4$-Cl, $X_4=H$ Prepared by the procedure of Example 58.

Crystals melting at 210°–211° C.

EXAMPLE 154

Ethyl 4-[1-(4-chlorobenzyl)imidazo[4,5-b]pyridin-2-yl]-3,3-dimethylbutanoate

Formula (I): $R_1=R_2=CH_3$, $R_3=R_4=H$, $n=1$, $D=CO_2Et$, $A=2$-pyridine, $B=CH_2$, $X_1=X_2=H$, $X_3=H$, $X_4=4$-Cl Prepared by the procedure of Example 91.

Oil used as such for the next step.

EXAMPLE 155

4-[1-(4-Chlorobenzyl)imidazo[4,5-b]pyridin-2-yl]-3,3-dimethylbutanoic acid

Formula (I): $R_1=R_2=CH_3$, $R_3=R_4=H$, $n=1$, $D=CO_2H$, $A=2$-pyridine, $B=CH_2$, $X_1=X_2=H$, $X_3=H$, $X_4=4$-Cl Prepared by the procedure of Example 58.

Crystals melting at 138°–140° C.

EXAMPLE 156

5-Formyl-4,4-dimethylvaleronitrile

Formula (VIII'): $R_1=R_2=CH_3$, $R_3=R_4=R_6=R=H$, $n=2$, $D=CN$

A] Ethyl 4-(dioxolan-2-yl)-3,3-dimethylbutanoate 74 g of ethyl 4-formyl-3,3-dimethylbutanoate, prepared in Example 91, are dissolved in 450 ml of anhydrous toluene in the presence of 0.5 g of paratoluenesulfonic acid and 26.7 g of ethylene glycol. The mixture is heated to the reflux temperature and the water formed during the reaction is removed by means of a Dean-Stark apparatus. After refluxing for two hours, the solvent is evaporated off under vacuum and the residue is distilled to give 86.7 g of ethyl 4-(dioxolan-2-yl)-3,3-dimethylbutanoate in the form of a liquid with a boiling point b.p. of 138°–140° C.

B] 4-(Dioxolan-2-yl)-3,3-dimethylbutanol 86.7 g of ethyl 4-(dioxolan-2-yl)-3,3-dimethylbutanoate, prepared above, are dissolved in 720 ml of ether. This solution is added dropwise at 10° C. to a suspension of 9 g of lithium aluminum hydride in 700 ml of ether. When the addition is complete, the mixture is stirred for 3 hours at room temperature and then cooled to 10° C. A saturated solution of sodium sulfate is added dropwise at this temperature until a granular precipitate is obtained, which is filtered off. The ether filtrate is evaporated to dryness at a temperature below 30° C. to give 81.9 g of 4-(dioxolan-2-yl)-3,3-dimethylbutanol in the form of an oil, which is used as such for the next step.

C] 4-(Dioxolan-2-yl)-3,3-dimethylbutanol mesylate 81.9 g of 4-(dioxolan-2-yl)-3,3-dimethylbutanol, prepared above, are dissolved in 600 ml of chloroform, stabilized with amylene, in the presence of 62 ml of triethylamine. The mixture is cooled to 5° C. and 81 ml of mesyl chloride are added dropwise. The mixture is subsequently stirred for 4 hours at 5° C. and then left overnight at this temperature, washed with cold water and evaporated at 30° C. under vacuum. The residue obtained is taken up with ether and washed with sodium bicarbonate. The ether phase is dried over magnesium sulfate and then evaporated at 30° C. under vacuum to give 93.5 g of 4-(dioxolan-2-yl)-3,3-dimethylbutanol mesylate.

D] 5-(Dioxolan-2-yl)-4,4-dimethylvaleronitrile 93.5 g of the mesylate prepared in C]are dissolved in 500 ml of acetonitrile. 50 g of potassium cyanide and 4.8 g of crown ether 18°-6 are added. The mixture is refluxed for 8 hours and then taken up with water and extracted with ethyl acetate. The organic phase is washed several times with water and then dried over magnesium sulfate and evaporated under vacuum. The residue obtained is distilled under reduced pressure to give 50 g of 5-(dioxolan-2-yl)-4,4-dimethylvaleronitrile with a boiling point b.p.$^{0.5}$ of 90°-8° C.

E] 5-Formyl-4,4-dimethylvaleronitrile 50 g of 5-(dioxolan-2-yl)-4,4-dimethylvaleronitrile, prepared in D], are dissolved in 1.3 l of acetone in the presence of 140 ml of concentrated hydrochloric acid and 700 ml of water. The mixture is stirred at room temperature for 5 hours, the acetone is concentrated under vacuum and the residue is taken up with ether, washed with water and then evaporated to dryness to give 35 g of 5-formyl-4,4-dimethylvaleronitrile.

EXAMPLE 157

5-[1-(4-Chlorobenzyl)-5-fluorobenzimidazol-2-yl]-4,4-dimethylvaleronitrile

Formula (I): $R_1=R_2=CH_3$, $R_3=R_4=H$, $n=2$, $D=CN$, $A=$phenyl, $B=CH_2$, $X_1=5$-F, $X_2=X_3=H$, $X_4=4$-Cl Prepared by the procedure of Example 91 from 5-formyl-4,4-dimethylvaleronitrile prepared in Example 156.

Oil used as such for the next step.

EXAMPLE 158

5-[1-(4-Chlorobenzyl)-5-fluorobenzimidazol-2-yl]-4,4-dimethylpentanoic acid

Formula (I): $R_1=R_2=CH_3$, $R_3=R_4=H$, $n=2$, $D=CO_2H$, $X_1=5$-F, $X_2=H$, $X_3=H$, $X_4=4$-Cl, $B=CH_2$, $A=$phenyl 3 g of 5-[1-(4-chlorobenzyl)-5-fluorobenzimidazol-2-yl]-4,4-dimethylvaleronitrile, prepared in Example 157, are dissolved in a mixture composed of 30 ml of water and 30 ml of ethanol. 3 g of sodium hydroxide pellets are added and the mixture is refluxed for 15 hours. After cooling, 100 ml of water are added and the solution obtained is washed with ether. The aqueous phase is acidified by having sulfur dioxide bubbled through it and the crystals obtained are filtered off, washed with water and then with isopropyl ether and dried to give 2.3 g of 5-[1-(4-chlorobenzyl)-5-fluorobenzimidazol-2-yl]-4,4-dimethylpentanoic acid in the form of crystals melting at 184°-6° C.

EXAMPLE 159

Acid chloride ethyl ester of cyclohexene-cis-4,5-dicarboxylic acid

Formula (VIII): $n=0$, $D=CO_2Et$, $R_1=R_5=H$, $R_6+R_2=CH_2-CH=CH-CH_2$

Prepared by the procedure of Example 28 from cyclohexene-cis-4,5-dicarboxylic anhydride.

Oil used as such for the next step.

EXAMPLE 160

Ethyl cis-5-[1-(4-chlorobenzyl)-5-fluorobenzimidazol-2-yl]cyclohexene-4-carboxylate Formula (I): $B=CR_5R$, $R_1=R_5=H$, $R_2+R_6=CH_2-CH=CH-CH_2$, $n=0$, $D=CO_2Et$, $A=$phenyl, $X_1=5$-F, $X_2=X_3=H$, $X_4=4$-Cl Prepared by the procedure of Example 34.

Crystals melting at 136° C.

EXAMPLE 161

Cis-5-[1-(4-chlorobenzyl)-5-fluorobenzimidazol-2-yl]cyclohexene-4-carboxylic acid Formula (I): $B=CR_5R_6$, $R_1=R_5=H$, $R_2+R_632 CH_2-CH=CH-CH_2$, $n=0$, $D=CO_2H$, $A=$phenyl, $X_1=5$-F, $X_2=X_3=H$, $X_4=4$-Cl Prepared by the procedure of Example 58.

Crystals melting at 185°-186° C.

EXAMPLE 162

2-(4-Methylthiobenzyl)amino-3-nitro-5-chloropyridine

Formula (V): $X_1=5$-Cl, $X_2=H$, $X_3=4$-SCH$_3$, $X_4=H$, $A=2$-pyridine

Prepared by the procedure of Example 6.

Crystals melting at 88° C.

EXAMPLE 163

2-(4-Methylthiobenzyl)amino-3-amino-5-chloropyridine

Formula (IV): $X_1=5$-Cl, $X_2=H$, $X_3=4$-SCH$_3$, $X_4=H$, $A=2$-pyridine

Prepared by the procedure of Example 14.

Crystals melting at 116° C.

EXAMPLE 164

Ethyl 4-[1-(4-methylthiobenzyl)-5-chloroimidazo[4,5-b]pyridin-2 yl]-3,3-dimethylbutanoate Formula (I): $R_1=R_2=CH_3$, $R_3=R_4=H$, $n=1$, $D=CO_2Et$, $A=2$-pyridine, $B=CH_2$, $X_1=5$-Cl, $X_2=X_3=H$, $X_4=4$-SCH$_3$ Prepared by the procedure of Example 91.

Oil used as such for the next step.

EXAMPLE 165

4-[1-(4-Methylthiobenzyl)-5-chloroimidazo[4,5-b]pyridin-2 yl]-3,3-dimethylbutanoic acid Formula (I): $R_1=R_2=CH_3$, $R_3=R_4=H$, $n=1$, $D=CO_2H$, $A=2$-pyridine, $B=CH_2$, $X_2=X_1=5$-Cl, $X_2=X_3=H$, $X_4=4$-SCH.$_3$ Prepared by the procedure of Example 92.

Crystals melting at 125°-126° C.

TABLE

Example 58    UP 116-52

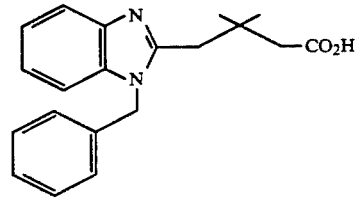

TABLE-continued
| Example 59 | 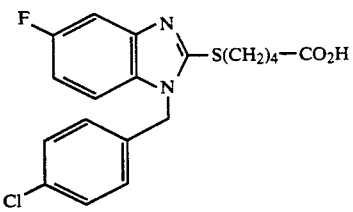 | UP 116-11 |
| Example 60 | 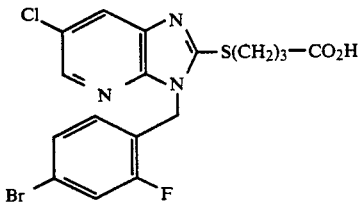 | UP 116-17 |
| Example 61 | 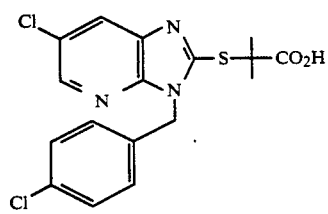 | UP 116-21 |
| Example 62 | 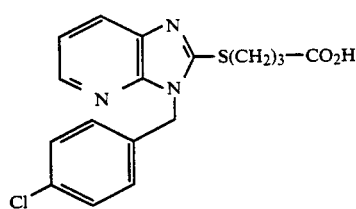 | UP 116-13 |
| Example 63 | 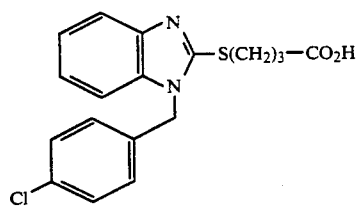 | UP 116-16 |
| Example 64 | 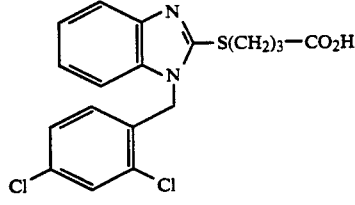 | UP 116-18 |
| Example 65 | 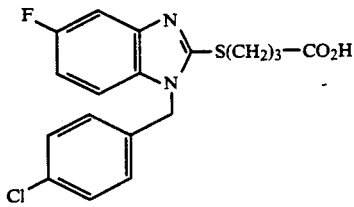 | UP 116-1 |

TABLE-continued
Example 66 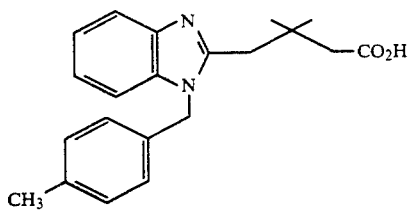 UP 116-57
Example 67 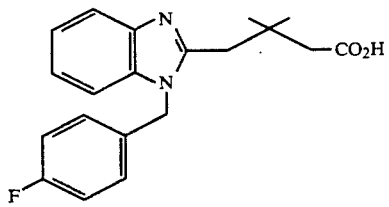 UP 116-56
Example 68 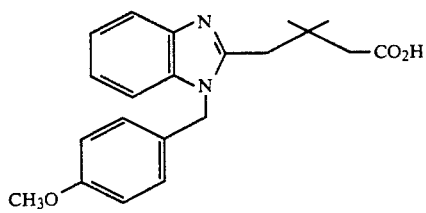 UP 116-55
Example 69 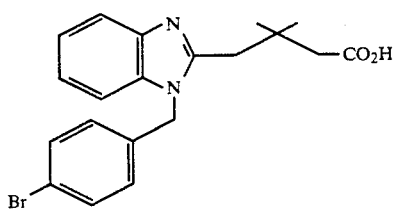 UP 116-59
Example 70 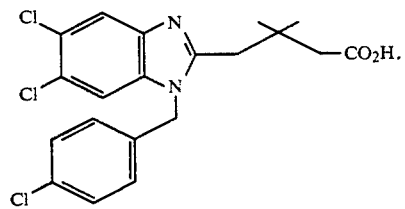 UP 116-63
Example 71 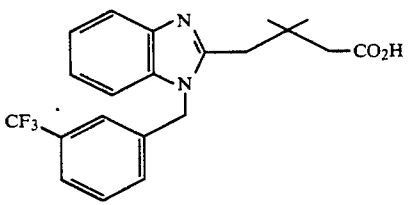 UP 116-67
Example 72 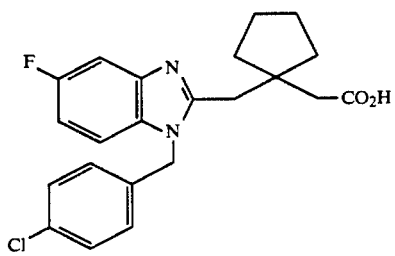 UP 116-53

TABLE-continued
| Example 73 | 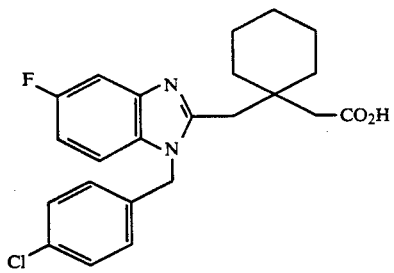 | UP 116-54 |
| --- | --- | --- |
| Example 74 | 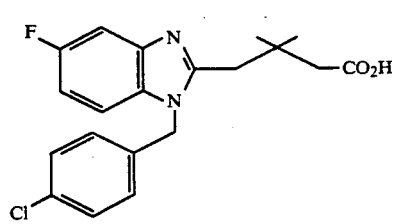 | UP 116-47 |
| Example 75 | 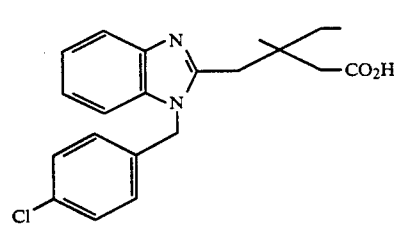 | UP 116-65 |
| Example 76 | 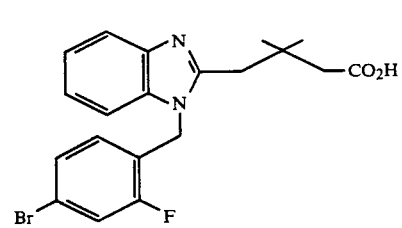 | UP 116-51 |
| Example 77 | 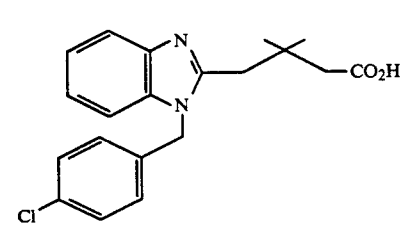 | UP 116-58 |
| Example 78 | 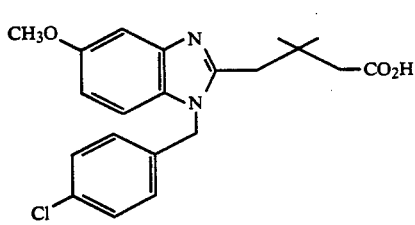 | UP 116-64 |
| Example 79 | 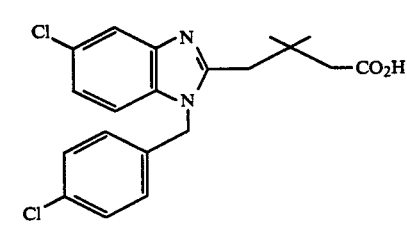 | UP 116-60 |

TABLE-continued
| Example 80 | 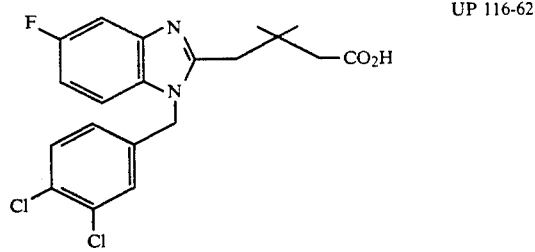 | UP 116-62 |
| Example 81 | 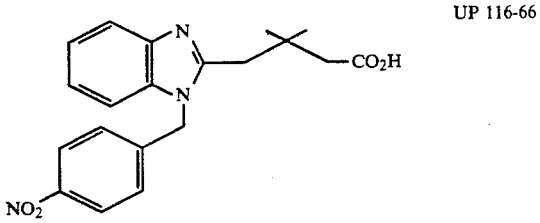 | UP 116-66 |
| Example 82 | 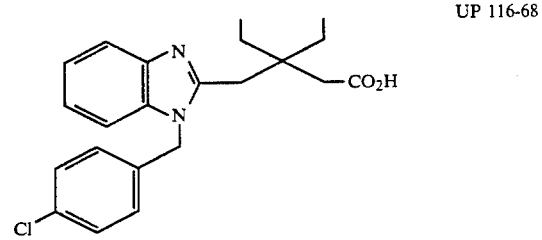 | UP 116-68 |
| Example 83 | 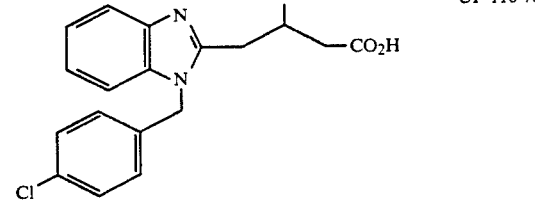 | UP 116-70 |
| Example 84 | 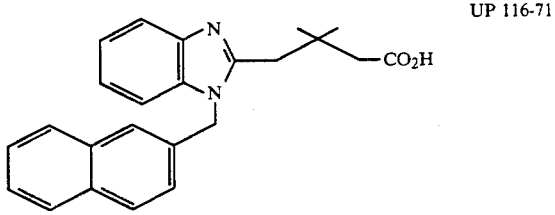 | UP 116-71 |
| Example 85 | 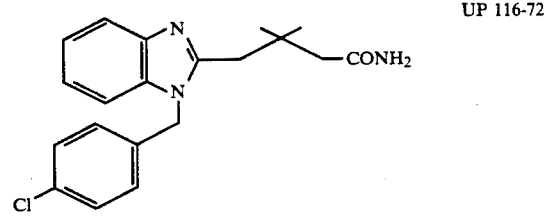 | UP 116-72 |
| Example 86 | 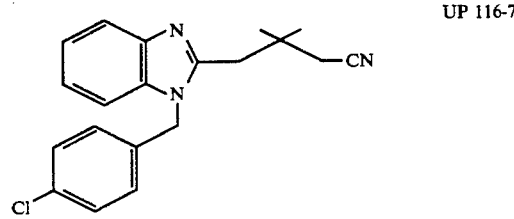 | UP 116-73 |

TABLE-continued
| | | |
|---|---|---|
| Example 87 | 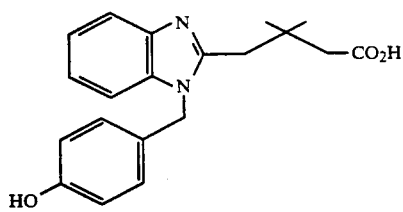 | UP 116-61 |
| Example 90 | 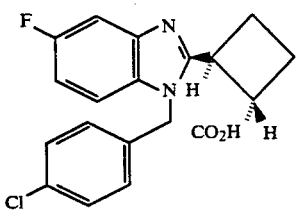 | UP 116-74 |
| Example 92 | 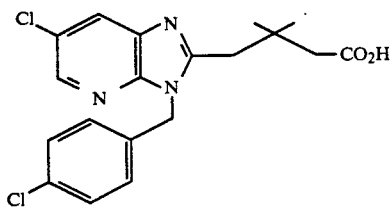 | UP 116-77 |
| Example 96 | 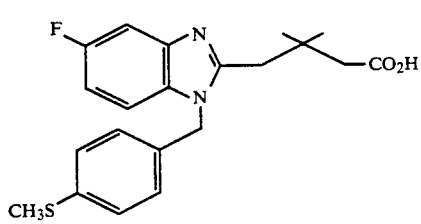 | UP 116-78 |
| Example 97 | 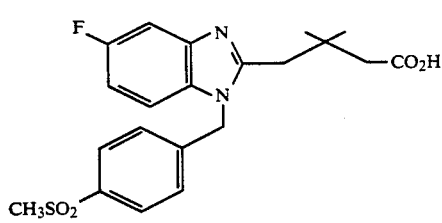 | UP 116-79 |
| Example 101 | 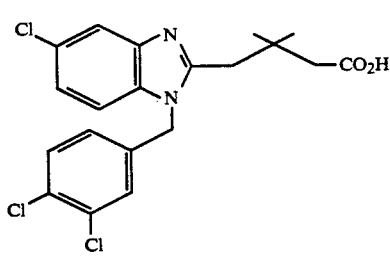 | UP 116-81 |
| Example 105 | 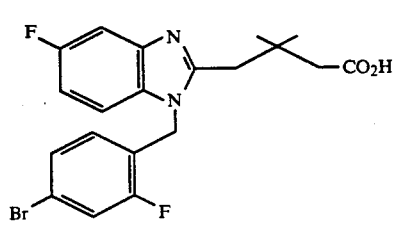 | UP 116-83 |

TABLE-continued
| Example 109 | 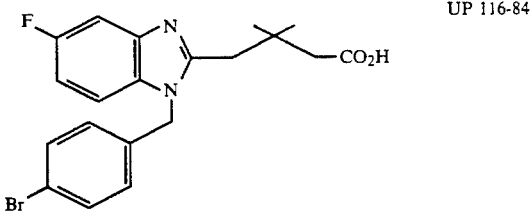 | UP 116-84 |
| Example 117 | 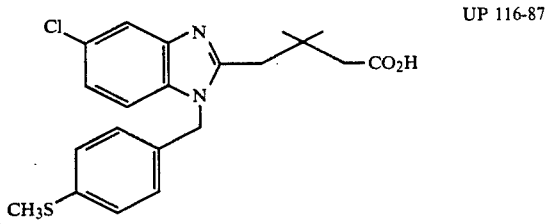 | UP 116-87 |
| Example 118 | 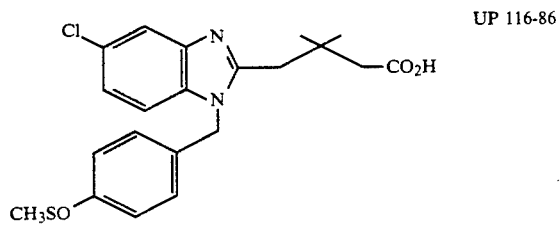 | UP 116-86 |
| Example 119 | 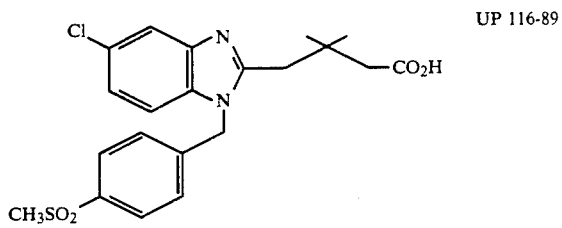 | UP 116-89 |
| Example 123 | 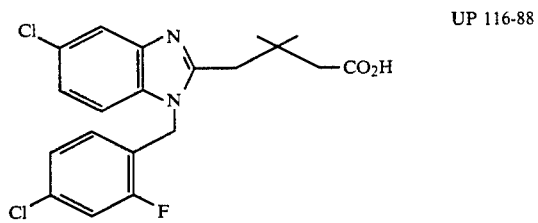 | UP 116-88 |
| Example 127 | 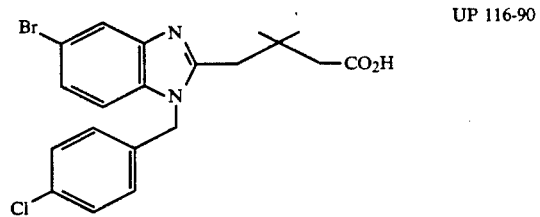 | UP 116-90 |
| Example 131 | 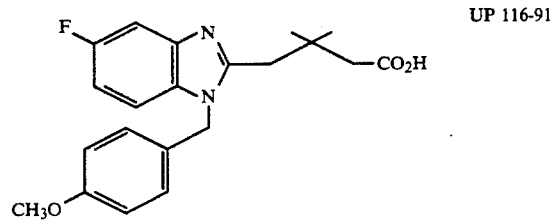 | UP 116-91 |

TABLE-continued
| | | |
|---|---|---|
| Example 135 | 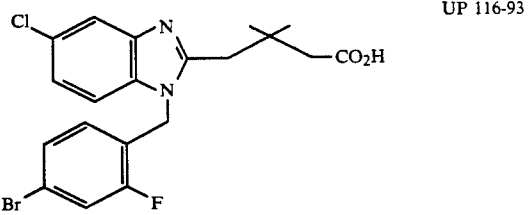 | UP 116-93 |
| Example 139 | 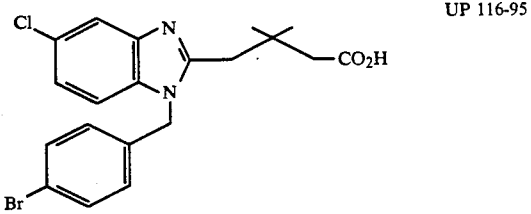 | UP 116-95 |
| Example 143 | 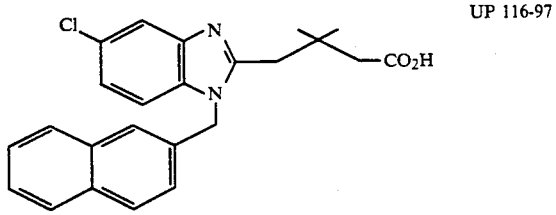 | UP 116-97 |
| Example 147 | 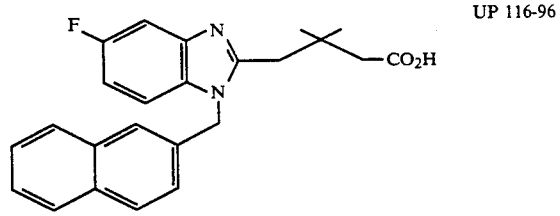 | UP 116-96 |
| Example 150 | 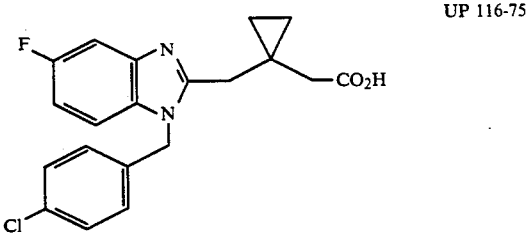 | UP 116-75 |
| Example 153 | 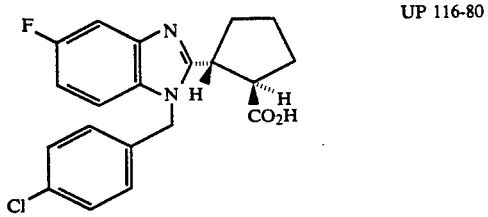 | UP 116-80 |
| Example 155 | 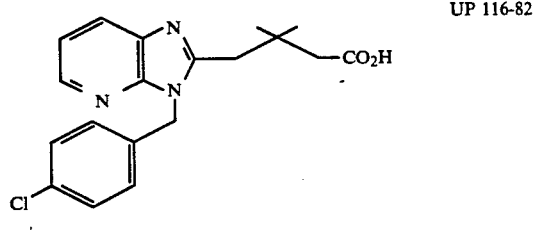 | UP 116-82 |

TABLE-continued

Example 158 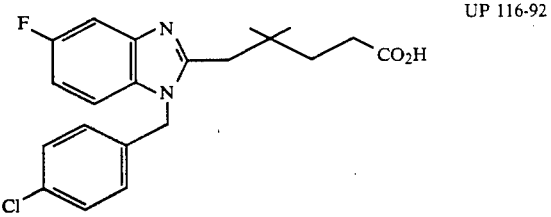 UP 116-92

Example 161 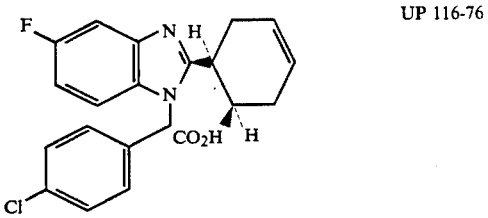 UP 116-76

Example 113 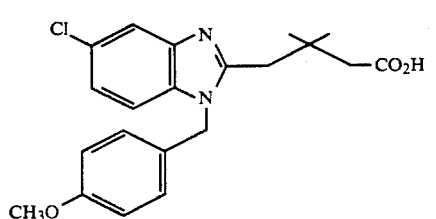 UP 116-85

Example 165 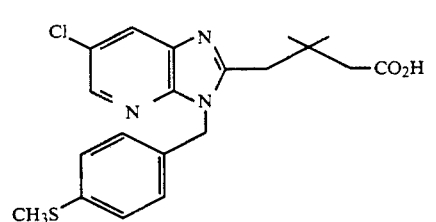 UP 116-99

PHARMACOLOGY

Principle

The affinity of the products of the Examples described for thromboxane $A_2$ receptors is evaluated by the technique of displacing a radioligand specifically bound to the $TXA_2$ receptors of human platelets.

Technique

Human platelets incubate in the presence of a single concentration of $[^{125}I]$PTA-OH (9,11-dimethylmethano-11,12-methano-16-(3-$[^{125}I]$iodo-4-hydroxyphenyl)-13,14-dihydro-13-aza-15α-ω-tetranor-$TXA_2$), a $TXA_2/PGH_2$ receptor antagonist, and two concentrations of competing agents ($10^{-5}$ M, $10^{-7}$ M) for 30 minutes at 37° C.

The reaction is completed by the addition of a buffer, followed by rapid filtration through glasspaper filters.

The non-specific binding is determined in the presence of U 46619 (9,11-dideoxy-11α,9α-epoxymethanoprostaglandin $F_{2α}$; mimetic thromboxane $A_2$).

Results

The results are expressed, for the doses tested, as the percentage displacement of the radioligand specifically bound to the $TXA_2$ receptors of human platelets. For certain products of the Examples, the inhibition constant Ki was determined according to the formula of CHENG and PRUSOFF:

$$Ki = \frac{IC_{50}}{1 + \frac{L}{K_D}}$$

in which IC denotes the 50% inhibitory concentration, L the concentration of radioactive ligand and $K_D$ the dissociation constant of the radioactive ligand.

Toxicology

Preliminary toxicity studies were able to show that the 50% lethal doses determined after oral administration to rats were greater than 300 mg/kg, representing an advantageous therapeutic index.

Conclusion

In conclusion, the molecules described in the present patent application, or their non-toxic addition salts, exhibit a substantial affinity for $TXA_2$ receptors and can be advantageously and profitably used in the treatment of the following pathological conditions:

myocardial infarction, angina pectoris, stroke, migraine, cerebral hemorrhage, atherosclerosis, pulmonary embolism, bronchial asthma, bronchitis, pneumonia, circulatory shock of various origins (hemorrhage, septicemia, heart failure, trauma, acute pancreatitis, burn, bacterial origin), nephritis, graft rejection and cancerous metastases, by oral administration in the form of tablets or gelatin capsules containing from 1 to 200 mg of active ingredient, or by parenteral administration in the form of injectable preparations containing from 0.01 to 10 mg of active ingredient, preferably in several dosage units (2 to 4) or administrations per day.

| Example | % displacement | |
|---|---|---|
| | Concentration 1E-7 M | Concentration 1E-5 M |
| 58 | 13 | 95 |
| 59 | 28 | 100 |
| 60 | 24 | 60 |
| 61 | 30 | 100 |
| 62 | 27 | 64 |
| 63 | 37 | 97 |
| 64 | 34 | 97 |
| 65 | 8 | 93 |
| 66 | 52 | 100 |
| 67 | 66 | 100 |
| 68 | 89 | 100 |
| 69 | 86 | 96 |
| 70 | 14 | 100 |
| 71 | 49 | 100 |
| 72 | 71 | 100 |
| 73 | 0 | 98 |
| 74 | 94 | 100 |
| 75 | 57 | 100 |
| 76 | 88 | 99 |
| 77 | 85 | 100 |
| 78 | 44 | 100 |
| 79 | 74 | 99 |
| 80 | 89 | 92 |
| 81 | 83 | 100 |
| 82 | 35 | 97 |
| 83 | 10 | 100 |
| 84 | 85 | 98 |
| 85 | 7 | 90 |
| 87 | 50 | 96 |
| 90 | 2 | 97 |
| 92 | 97 | 100 |
| 96 | 100 | 100 |
| 97 | 100 | 100 |
| 101 | 71 | 92 |
| 105 | 100 | 98 |
| 109 | 95 | 92 |
| 117 | 87 | 89 |
| 118 | 54 | 92 |
| 119 | 61 | 82 |
| 123 | 77 | 87 |
| 127 | 38 | 67 |
| 131 | 79 | 100 |
| 135 | 74 | 95 |
| 139 | 98 | 100 |
| 143 | 77 | 89 |
| 147 | 91 | 93 |
| 150 | 80 | 98 |
| 153 | 37 | 100 |
| 155 | 41 | 62 |
| 158 | 56 | 87 |
| 161 | 15 | 96 |

| Product of Example | Ki (M/l) |
|---|---|
| 68 | $3.10 \times 10^{-8}$ |
| 69 | $1.58 \times 10^{-8}$ |
| 72 | $4.23 \times 10^{-8}$ |
| 73 | $8.07 \times 10^{-7}$ |
| 74 | $6.30 \times 10^{-9}$ |
| 76 | $1.14 \times 10^{-8}$ |
| 77 | $3.10 \times 10^{-8}$ |
| 79 | $2.32 \times 10^{-8}$ |
| 80 | $6.02 \times 10^{-9}$ |
| 81 | $6.01 \times 10^{-8}$ |
| 90 | $1.18 \times 10^{-6}$ |
| 92 | $1.25 \times 10^{-8}$ |
| 96 | $5.00 \times 10^{-9}$ |
| 97 | $3.70 \times 10^{-8}$ |
| 105 | $1.50 \times 10^{-8}$ |
| 117 | $5.80 \times 10^{-9}$ |
| 139 | $1.30 \times 10^{-8}$ |

What is claimed is:

1. A benzimidazole derivative selected from the group consisting of:

a) compounds of formula (I):

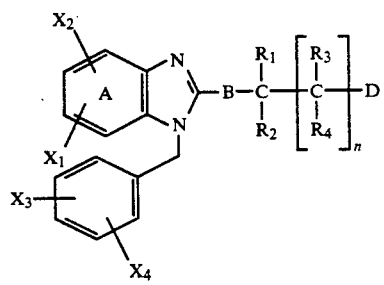

in which:

A is a phenyl or naphthyl group;

$X_1$, $X_2$, $X_3$ and $X_4$ are independently a hydrogen atom, a halogen atom, a lower alkyl radical, a $C_3-C_7$ cycloalkyl radical, a $C_1-C_6$ alkoxy group radical, a $C_1-C_6$ alkylthio group, a sulfane group, $SO_2$-lower alkyl, a sulfoxide group, SO-lower alkyl, a trifluoromethyl group, a hydroxyl group, a nitro group, a methylene alcohol radical or a group COOR', in which R' is a hydrogen or a lower alkyl; $X_3$ and $X_4$ can also form a naphthalene with the phenyl; with the proviso that at least one of $X_1$, $X_2$, $X_3$ and $X_4$ SO-lower alkyl or SO-lower alkyl;

B is $CR_5R_6$, $R_5$ and $R_6$ being a hydrogen atom, a lower alkyl group or a $C_3-C_7$ cycloalkyl group, or the sulfur atom;

$R_1$, $R_2$, $R_3$ and $R_4$ are independently a hydrogen atom, a lower alkyl radical or a $C_3-C_7$ cycloalkyl radical; $CR_1C_2$ or $CR_3R_4$ can form with B, when the later is $CR_5R_6$, a cycloalkyl or a cycloalkene having 3 to 7 carbon atoms; $R_1R_2$ or $R_3R_4$ can also form a cycloalkyl group having 3 to 7 carbon atoms;

n is an integer from 1 to 4 and can be 0 if $R_1$ and $R_2$ are other than hydrogen; and D is a chemical group which can be:
  $COOR_7$, $R_7$ being the hydrogen atom, a lower alkyl group or a $C_3-C_7$ cycloalkyl group.
  $COHN-R_8$, $R_8$ being the hydrogen atom, a lower alkyl group or a $C_3-C_7$ cycloalkyl group, or CN b) compounds selected from the group consisting of:
Ethyl 4-[1-(4-methylthiobenzyl)-5-fluorobenzimidozol-2-yl ]-3,3-dimethylbutanoate
4-[1-(4-Methylthiobenzyl)-5-fluorobenzimidazol-2-yl]-3,3dimethylbutanoic acid
Ethyl 4-]1-(3,4-dichlorobenzyl)-5-chlorobenzimidazol-2-yl]-3,3-dimethylbutanoate
4-[1(3,4-Dichlorobenzyl)-5-chlorobenzimidazol-2-yl]-3,3-dimethylbutanoic acid
Ethyl 4-[1-(2-fluoro-4-bromobenzyl)-5flurobenzimidazol-2-yl]-3,3-dimethylbutanoate
4-[1(2-Fluoro-4-bromobenzyl)-5-fluorobenzimidazol-2-yl]-3,3-dimethylbutanoic acid Ethyl 4-[1-(4-bromobenzyl)-5-fluorobenzimidazol-2-yl]-3,3-dimethylbutanoate
4-[1-(4-Bromobenzyl)-5-fluorobenzimidazol-2-ul]-3,3-dimethylbutanoic acid
Ethyl 4-[1-(4-methoxybenzyl)-5-chlorobenzimidazol-2-yl]-3,3-dimethylbutanoate
4-[1-(4-Methoxybenzyl)-5-chlorobenzimidazol-2-yl]-3,3-dimethylbutanoic acid
Ethyl 4-[1-(4-methylthiobenzyl(-5-chlorobenzimidazol-2-yl ]-3,3-dimethylbutanoate
4-[1(4-Methylthiobenzyl)-5-chlorobenzimidazol-2-yl]-3,3-dimethylbutanoic acid
Ethyl 4-[1-(2-fluoro-4-chlorobenzyl)-5-chlorobenzimidazol-2-yl]-3,3-dimethylbutanoate
4-[1-(2-Fluoro-4-chlorobenzyl)-5-chlorobenzimidazol-2-yl]-3,3-dimethylbutanoic acid Ethyl 4-[1-(4-chlorobenzyl)-5-bromobenzimidazol-2-yl]-3,3-dimethylbutanoate
4-[1-(4-Chlorobenzyl)-5-bromobenzimidazol-2-yl]-3,3-dimethylbutanoic acid
Ethyl 4-[1(4-methoxybenzyl)-5-fluorobenzimidazol-2-yl]-3,3-dimethylbutanoate
Ethyl 4-[1-(2-fluoro-4-bromobenzyl)-5-chlorobenzimidazol-2-yl]-3,3-dimethylbutanoate
4-[1-(2-Fluoro-4-bromobenzyl)-5-chlorobenzimidazol-2-yl]-3,3-dimethylbutanoic acid
Ethyl 4-[1-(4-bromobenzyl)-5-chlorobenzimidazol-2-yl]-3,3-dimethylbutanoate
4-[1-(4-Bromobenzyl)-5-chlorobenzimidazol-2-yl]-3,3-dimethylbutanoic acid
Ethyl 4-[1-(naphth-2-ylmethyl)-5-chlorobenzimidazol-2-yl]-3,3-dimethylbutanoate
4-[1-(Naphth-2-ylmethyl)-5-chlorobenzimidazol-2-yl]-3,3-dimethylbutanoic acid
Ethyl 4-[1-(naphth-2-ylmethyl)-5-fluorobenzimidazol-2-yl]-3,3-dimethylbutanoate
4-[1-(Naphth-2-ylmethyl)-5-fluorobenzimidazol-2-yl]-3,3-dimethylbutanoic acid
Ethyl [1-[1-(4-chlorobenzyl)-5-fluorobenzimidazol-2-yl ]methylcycloprop-1-yl]acetate
[1-[1-(4-Chlorobenzyl)-5-fluorobenzimidazol-2-yl]-methylcycloprop-1-yl]acetic acid
Ethyl trans-2-[1-(4-chlorobenzyl)-5-fluorobenzimidazol-2-yl]cyclopentane-1-carboxylate
Trans-2-[1-(4-chlorobenzyl)-5-fluorobenzimidazol-2-yl]cyclopentane-1-carboxylic acid
5-[1-(4-Chlorobenzyl)-5-fluorobenzimidazol-2-yl]-4,4-dimethylvaleronitrile
5-[1-(4-Chlorobenzyl)-5-fluorobenzimidazol-2-yl]-4,4-dimethylpentanoic acid
Ethyl cis-5-[1-(4-chlorobenzyl)-5-fluorobenzimidazol-2-yl]cyclohexene-4-carboxylate
Cis-5-[1-(4-chlorobenzyl)-5-fluorobenzimidazol-2-yl]-cyclohexene-4-carboxylic acid.

2. A derivative according to claim 1, wherein A is a phenyl ring.
3. A derivative according to claim 1, wherein $X_1$ is the fluorine atom.
4. A derivative according to claim 1, wherein $X_1$ is the chlorine atom.
5. A derivative according to claim 1, wherein $X_4$ is the methylsulfonyl group.
6. A derivative according to claim 1, wherein $X_4$ is the methylsulfoxy group.
7. A derivative according to claim 1, wherein $X_4$ is the chlorine atom.

8. A derivative according to claim 1, wherein D is an acid group.
9. A derivative according to claim 1, wherein B is a methylene group, $R_1$ and $R_2$ are each a methyl, $R_3$ and $R_4$ are hydrogen and n is equal to 1.
10. A derivative according to claim 1, wherein B is the sulfur atom.
11. A derivative according to claim 1, wherein $CR_1R_2$ is a cyclopentane.
12. A derivative according to claim 1 which is selected from the derivatives of the formulae:

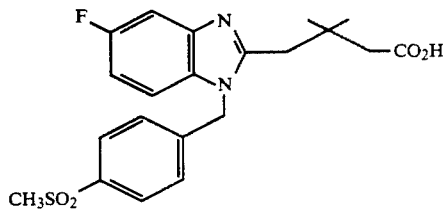

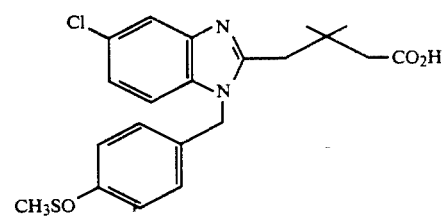

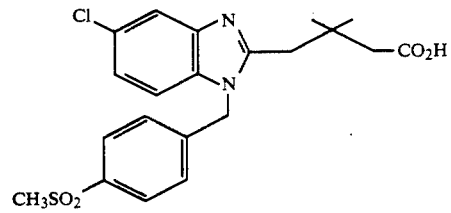

13. A method of preparing the compounds of formula (I) according to claim 1, wherein said compounds are prepared:

A if B is a sulfur atom: by reacting an alkyl halogenoalkanoate with a mercaptobenzimidazole or mercaptoazabenzimidazole in the presence of a base such as a sodium or potassium alcoholate, sodium or lithium hydride of potassium carbonate, in an alcohol, dimethylformamide, acetone or butan-2-one; or B is B is a group $CR_5R_6$: in two steps by reacting an acid chloride of formula (VIII):

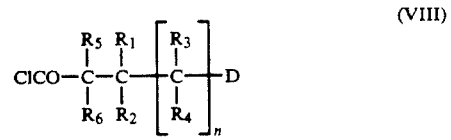

(VIII)

in which $R_1$, $R_2$, $R_3$, $R_4$, $R_5$, $R_6$ and n are as defined above and D is an ester or nitrile group, with a diamine of formula (IV):

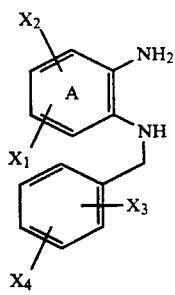
(IV)

in which A, $X_1$, $X_2$, $X_3$ and $X_4$ are as defined above, this being followed in a second stage by cyclization in an acid medium, or by reacting the diamine of formula (IV) with an aldehyde of formula (VIII'):

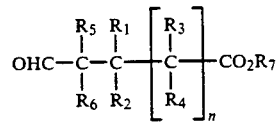
(VIII')

in which $R_1$, $R_2$, $R_3$, $R_4$, $R_5$, $R_6$ and n are as defined above and $R^7$ is a lower alkyl radical, in an acetic acid and alcohol medium, it being possible for said alcohol to be methanol, ethanol or methoxyethanol for example, the derivative obtained then being oxidized with an oxidizing agent such as iodine or barium manganate, acid or basic hydrolysis of the ester or nitrile derivatives yielding the acid derivatives.

14. A pharmaceutical composition which comprises a pharmaceutically effective amount of a compount of formula (I) as defined in claim 1, or one of its pharmaceutically acceptable addition salts, incorporated in a pharmaceutically acceptable excipient, vehicle or carrier.

15. A pharmaceutical composition which contains, as the active principal, an effective thromboxane receptor antagonist amount of a compound of formula (1) as defined in claim 1, or one of its pharmaceutically acceptable carriers.

* * * * *